United States Patent [19]

Hamprecht et al.

[11] Patent Number: 5,262,384
[45] Date of Patent: Nov. 16, 1993

[54] PYRIDINE DERIVATIVES AND THEIR USE FOR CONTROLLING UNDESIRABLE PLANT GROWTH

[75] Inventors: Gerhard Hamprecht, Weinheim; Norbert Goetz, Worms; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 825,793

[22] Filed: Jan. 21, 1992

Related U.S. Application Data

[63] Continuation-in-part of Ser. No. 594,934, Oct. 10, 1990, abandoned.

[30] Foreign Application Priority Data

Oct. 10, 1989 [DE] Fed. Rep. of Germany ....... 3933802

[51] Int. Cl.$^5$ .................. A01N 43/90; C07D 47/04
[52] U.S. Cl. .................. 504/225; 504/239; 504/246; 544/127; 544/333; 546/113
[58] Field of Search ............ 546/113; 544/127, 333; 71/92, 94; 504/239, 225, 246

[56] References Cited

U.S. PATENT DOCUMENTS

| | | | |
|---|---|---|---|
| 3,525,747 | 8/1970 | Jacobs | 546/113 |
| 3,539,568 | 11/1990 | Jacobs | 546/113 |
| 3,966,726 | 6/1976 | Toth et al. | 546/113 |
| 4,261,230 | 4/1981 | Bollinger et al. | 71/94 |
| 4,658,030 | 4/1982 | Barton et al. | 546/167 |
| 4,709,052 | 11/1987 | Tomiaka et al. | 548/548 |
| 4,754,033 | 6/1988 | Waldner | 546/113 |

FOREIGN PATENT DOCUMENTS

| | | |
|---|---|---|
| 0128006 | 12/1984 | European Pat. Off. . |
| 642582 | 3/1937 | Fed. Rep. of Germany . |
| 3122635 | 12/1982 | Fed. Rep. of Germany . |

OTHER PUBLICATIONS

Rice et al., J.A.C.S., 75, pp. 4911–4915 (1953).

Waldner, *Helvetica Chimica Acta*, 71, 486–496 (1988).

*Primary Examiner*—Bernard Dentz
*Attorney, Agent, or Firm*—Keil & Weinkauf

[57] ABSTRACT

Pyridine derivatives of the formulae

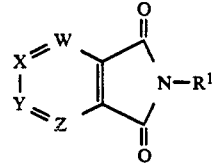

Ia

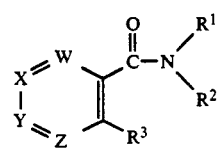

Ib

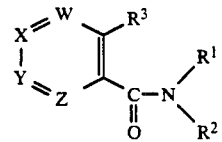

Ic where
W, X, Y and Z are each C—R$^4$, N or N→O, with the proviso that the ring contains only one heteroatom, and the substituents R$^1$, R$^2$ and R$^3$ have the following meanings:
R$^1$ is alkoxy, substituted or unsubstituted alkyl, substituted or unsubstituted cycloalkyl, substituted or unsubstituted alkenyl, or substituted or unsubstituted alkynyl,
R$^2$ is hydrogen,
R$^3$ is formyl, 4,5-dihydrooxazol-2-yl or —CO—A—R$^5$ or —CO—NR$^6$R$^7$,
where
R$^4$ is halogen, nitro, cyano, substituted or unsubstituted alkyl, substituted or unsubstituted benzyl, substituted or unsubstituted cycloalkyl, substituted or unsubstituted alkenyl, substituted or unsubsti- (Abstract continued on next page.)

tuted alkynyl, alkoxy, alkylthio, haloalkoxy, haloalkylthio, alkenyloxy, alkynyloxy, alkylsulfinyl, alkylsulfonyl, haloalkylsulfonyl, substituted or unsubstituted phenoxy or phenylthio, a substituted or unsubstituted 5- or 6-membered heterocyclic radical having one or two heteroatoms selected from the group consisting of oxygen, sulfur and nitrogen, or is substituted or unsubstituted phenyl A is oxygen or sulfur, $R^5$ is hydrogen, substituted or unsubstituted alkyl, substituted or unsubstituted benzyl, cycloalkyl, substituted or unsubstituted phenyl, one equivalent of a cation or the radical —N=CR$^8$R$^9$ and $R^6$ and $R^7$ are hydrogen or alkyl or together denote a methylene chain having 4 or 5 members, their agriculturally utilizable salts, and their use for controlling unwanted plant growth.

3 Claims, No Drawings

PYRIDINE DERIVATIVES AND THEIR USE FOR CONTROLLING UNDESIRABLE PLANT GROWTH

This application is a continuation-in-part application Ser. No. 07/594,934, filed on Oct. 10, 1990 now abandoned.

The present invention relates to novel pyridine derivatives, processes for their preparation and their use for controlling undesirable plant growth.

N-substituted pyridinedicarboximides and their derivatives are known. EP-A-128 006 describes, inter alia, N-cycloalkylenepyridinecarboximides and their use as soil fungicides.

DE-A-31 22 635 discloses 2,6-dichloropyridine-3,4-dicarboxylic acid N-alkylimides which are suitable as coupling components for azo dyes.

U.S. Pat. No. 3,539,568 describes a process for the preparation of 2,3- and 3,4-pyridinedicarboximides and their conversion into isomeric dicarboxamides, which can be used as intermediates for herbicidal pyrimidinediones.

U.S. Pat. No. 4,261,730 discloses 3-carboxypyridine-2-N-(aryl)-carboxamides and phthalamic acids having a growth-regulating action.

U.S. Pat. No. 4,658,030 discloses a process for the preparation of herbicidal 2-(imidazolin-2-yl)-nicotinic acids based on 3-carboxypyridin-2-(N-carbamido-3-methyl-2-butyl)-carboxamides.

Helv. Chim. Acta 71 (1988)1 486 and 493 discloses a cycloaddition process for the preparation of pyridine-2,3-dicarboximides. These substances are not known to have herbicidal properties.

We have found that pyridine derivatives of the formulae I′a, I′b and I′c

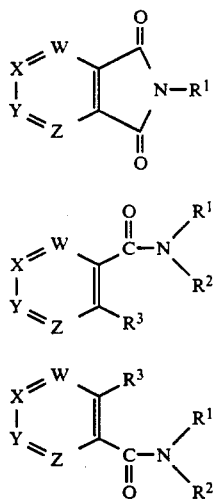

where

W, X, Y and Z are each $C-R^4$, N or $N \rightarrow O$, with the proviso that the ring contains only one hetero atom, and $R^1$ is hydrogen, hydroxyl, $C_1$–$C_4$-alkoxy, $C_1$–$C_6$-alkyl which may carry from one to three of the following groups:

$C_1$–$C_4$-alkoxy, $C_1$–$C_4$-haloalkoxy, $C_1$–$C_4$-alkylthio, $C_1$–$C_4$-haloalkylthio, $C_1$–$C_4$-dialkylamino, $C_3$–$C_8$-cycloalkyl, halogen, cyano, $C_3$–$C_8$-cycloalkyl or phenyl which may be substituted by halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$C_3$–$C_8$-cycloalkyl which may carry from one to three of the following groups: $C_1$–$C_6$-alkyl, $C_1$–$C_6$-haloalkyl, $C_1$–$C_4$-alkoxy, $C_1$–$C_4$-haloalkoxy, halogen, nitro or cyano;

$C_3$–$C_6$-alkenyl or $C_3$–$C_6$-alkynyl, each of which may be monosubstituted to trisubstituted by halogen and/or monosubstituted by phenyl which may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

$C_1$–$C_4$-dialkylamino;

a 5-membered or 6-membered heterocyclic radical having one or two heteroatoms selected from the group consisting of oxygen, sulfur and nitrogen, which may be up to trisubstituted by $C_1$–$C_4$-alkyl or halogen;

phenyl which may carry from one to four of the following groups: $C_1$–$C_4$-alkyl, $C_1$–$C_4$-haloalkyl, $C_1$–$C_4$-alkoxy, $C_1$–$C_4$haloalkoxy, $C_1$–$C_4$-alkylthio, $C_1$–$C_4$-haloalkylthio, halogen, nitro, cyano, formy, $C_2$–$C_5$-alkanoyl, $C_2$–$C_5$-haloalkanoyl or $C_2$–$C_5$-alkoxycarbonyl, or naphthyl which may be monosubstituted to trisubstituted by $C_1$–$C_4$-alkyl or halogen;

$R^2$ is hydrogen or $C_1$–$C_6$-alkyl which may carry from one to three of the following substituents: hydroxyl, halogen, $C_1$–$C_4$-alkoxy, $C_1$–$C_4$-alkylthio or $C_1$–$C_4$-dialkylamino; $C_3$–$C_8$-cycloalkyl which may be monosubstituted to trisubstituted by $C_1$–$C_4$-alkyl, halogen or $C_1$–$C_4$-haloalkyl, or $R^1$ and $R^2$ together form a radical having the structure $-(CH_2)_n-Y_p-(CH_2)_q-$, where n and q are each 1, 2 and 3, p is 0 or 1 and Y is oxygen or sulfur or N-methyl or the radical of the formula $-(CH_2)_3-CO-$;

$R^3$ is formyl, 4,5-dihydrooxazol-2-yl or one of the radicals $-COAR^5$ or $-CONR^6R^7$;

$R^4$ is hydrogen, halogen, nitro, cyano or $C_1$–$C_6$-alkyl which may be substituted by one to five halogen atoms and/or one or two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl or cyano;

benzyl which may be monosubstituted to trisubstituted by $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

$C_3$–$C_8$-cycloalkyl which may be monosubstituted to trisubstituted by $C_1$–$C_4$-alkyl or halogen;

$C_2$–$C_6$-alkenyl which may be monosubstituted to trisubstituted by halogen and/or monosubstituted by $C_1$–$C_3$-alkoxy or by phenyl which may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

$C_2$–$C_6$-alkynyl which may be monosubstituted to trisubstituted by halogen or $C_1$–$C_3$-alkoxy and/or monosubstituted by phenyl which may carry from one to three of the following groups: $C_1$–$C_4$-alkyl, $C_1$–$C_4$-haloalkyl, $C_1$–$C_4$-alkoxy, $C_1$–$C_4$haloalkoxy, $C_1$–$C_4$-alkylthio, $C_1$–$C_4$-haloalkylthio, halogen, cyano or nitro;

$C_1$–$C_4$-alkoxy, $C_1$–$C_4$-alkylthio, $C_1$–$C_4$-haloalkoxy, $C_1$–$C_4$-haloalkylthio, $C_2$–$C_5$-alkenyloxy, $C_2$–$C_5$- alkynyloxy, $C_1-C_4$-alkylsulfinyl, $C_1-C_4$-alkylsulfonyl or $C_1-C_4$-haloalkylsulfonyl;

phenoxy or phenylthio, each of which may be monosubstituted to trisubstituted by $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro;

a 5-membered or 6-membered heterocyclic radical having one or two heteroatoms selected from the group consisting of oxygen, sulfur and nitrogen, which may carry one or two substituents of the following groups: $C_1-C_3$-alkyl, halogen, $C_1-C_3$-alkoxy or $C_2-C_4$-alkoxycarbonyl, or phenyl which may carry from one to three of the following groups: $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, halogen, nitro or cyano;

A is oxygen or sulfur;

$R^5$ is hydrogen or $C_1-C_6$-alkyl which may be substituted by one to five halogen atoms or one to five hydroxyl groups and/or one of the following radicals: $C_1-C_4$-alkoxy, $C_1-C_4$-alkoxy-$C_2-C_4$-alkoxy, cyano, trimethylsilyl, $C_1-C_3$-alkylthio, $C_1-C_3$-alkylamino, $C_1-C_3$-dialkylamino, $C_1-C_3$-alkylsulfinyl, $C_1-C_3$-alkylsulfonyl, carboxyl, $C_1-C_3$-alkoxycarbonyl, $C_2-C_4$-alkoxycarbonyl-$C_1-C_3$-alkoxy, $C_2-C_4$-alkoxycarbonyl-$C_2-C_4$-alkoxycarbonyl, $C_1-C_3$-dialkylaminocarbonyl, $C_1-C_3$-dialkoxyphosphonyl, alkaniminoxy, thienyl, furyl, tetrahydrofuryl, phthalimido, pyridyl, benzyloxy or benzoyl which may carry from one to three of the following groups: $C_1-C_3$-alkyl, $C_1-C_3$-alkoxy or halogen;

benzyl which may carry from one to three of the following groups: $C_1-C_3$-alkyl, $C_1-C_3$-alkoxy, $C_1-C_3$-haloalkyl, halogen, nitro or cyano;

$C_3-C_8$-cycloalkyl;

phenyl which may carry from one to three of the following groups: $C_1-C_4$-alkyl, $C_1-C_4$-alkoxy, $C_1-C_4$-haloalkyl, $C_1-C_4$-haloalkoxy, $C_1-C_4$-alkoxycarbonyl, halogen, nitro or cyano; $C_3-C_8$-alkenyl, $C_5$- or $C_6$-cycloalkenyl, $C_3-C_8$-alkynyl, each of which may be monosubstituted by hydroxyl, $C_1-C_4$-alkoxy, halogen or phenyl, which may carry from one to three of the following groups: $C_1-C_4$-alkyl, $C_1-C_4$-alkoxyl $C_1-C_4$-haloalkyl, halogen, nitro or cyano;

a 5-membered or 6-membered heterocyclic radical having one or two heteroatoms selected from the group consisting of oxygen, sulfur and nitrogen, or benzotriazolyl;

phthalimido, tetrahydrophthalimido, succinimido or maleimido;

one equivalent of a cation from the group consisting of the alkali or alkaline earth metals, manganese, copper, iron, ammonium and substituted ammonium, or a radical $-N=CR^8R^9$, where $R^8$ and $R^9$ independently of one another are each hydrogen, $C_1-C_4$-alkyl, $C_3-C_6$-cycloalkyl, phenyl or furyl or together may form a methylene chain having 4 to 7 members;

$R^6$ is hydrogen, $C_1-C_6$-alkyl or $C_3-C_8$-cycloalkyl and $R^7$ is hydrogen or $C_1-C_6$-alkyl, or $R^6$ and $R^7$ may form a methylene chain having 4 or 5 members;

and salts thereof which can be used in agriculture possess herbicidal activity and are selective with respect to crops.

Pyridine derivatives of the formulae Ia, Ib and Ic

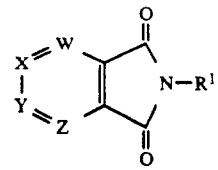

Ia

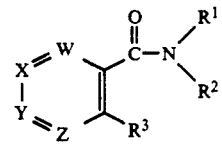

Ib

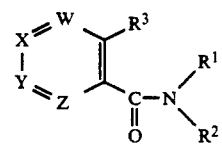

Ic where

W, X, Y and Z are each $C-R^4$, N or $N\to O$, with the proviso that the ring contains only one heteroatom, and $R^1$ is $C_1-C_4$-alkoxy or is $C_3-C_6$-alkyl which may carry from one to three of the following groups: $C_1-C_4$-alkoxy, $C_1-C_4$-haloalkoxy, $C_1-C_4$-alkylthio, $C_1-C_4$-haloalkylthio, $C_1-C_4$-dialkylamino, $C_3-C_8$-cycloalkyl or halogen, $C_1-C_8$-cycloalkyl which may carry from one to three of the following groups: $C_1-C_6$-alkyl, $C_1-C_6$-haloalkyl, $C_1-C_4$-alkoxy, $C_1-C_4$-haloalkoxy, halogen, nitro or cyano, $C_3-C_6$-alkenyl or $C_3-C_6$-alkynyl, each of which may be monosubstituted to trisubstituted by halogen, $R^2$ is hydrogen, $R^3$ is formyl, 4,5-dihydrooxazol-2-yl or one of the radicals $-CO-A-R^5$ or $-CO-NR^6R^7$, A is oxygen or sulfur, $R^4$ is halogen, nitro, cyano or $C_1-C_6$-alkyl which may be substituted by one to five halogen atoms and/or one or two of the following radicals: $C_1-C_4$-alkoxy, $C_1-C_4$-haloalkoxy, $C_1-C_4$-alkylthio, $C_1-C_4$-haloalkylthio, $C_3-C_6$-cycloalkyl or cyano, benzyl which may be monosubstituted to trisubstituted by $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, $C_3-C_8$-cycloalkyl which may be monosubstituted to trisubstituted by $C_1-C_4$-alkyl or halogen, $C_2-C_6$-alkenyl which may be monosubstituted to trisubstituted by halogen and/or monosubstituted by $C_1-C_3$-alkoxy or by phenyl which may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, $C_2-C_6$-alkynyl which may be monosubstituted to trisubstituted by halogen or $C_1-C_3$-alkoxy and/or monosubstituted by phenyl which may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, $C_1$–$C_4$-alkoxy, $C_1$–$C_4$-alkylthio, $C_1$–$C_4$-haloalkoxy, $C_1$–$C_4$-haloalkylthio, $C_2$–$C_5$-alkenyloxy, $C_2$–$C_5$-alkynyloxy, $C_1$–$C_4$-alkylsulfinyl, $C_1$–$C_4$-alkylsulfonyl or $C_1$–$C_4$-haloalkylsulfonyl, phenoxy or phenylthio, each of which may be monosubstituted to trisubstituted by $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro, a 5-membered or 6-membered heterocyclic radical having one or two heteroatoms selected from the group consisting of oxygen, sulfur and nitrogen, which may carry one or two substituents of the following groups: $C_1$–$C_3$-alkyl, halogen, $C_1$–$C_3$-alkoxy or $C_2$–$C_4$-alkoxycarbonyl, phenyl which may carry from one to three of the following groups: $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro or cyano, $R^5$ is hydrogen or $C_1$–$C_6$-alkyl which may be substituted by one to five halogen atoms or one to five hydroxyl groups and/or one of the following radicals: $C_1$–$C_4$-alkoxy, $C_1$–$C_4$-alkoxy-$C_2$–$C_4$-alkoxy, cyano or $C_1$–$C_3$-alkylthio, benzyl which may carry from one to three of the following groups: $C_1$–$C_3$-alkyl, $C_1$–$C_3$-alkoxy, $C_1$–$C_3$-haloalkyl, halogen, nitro or cyano, $C_3$–$C_8$-cycloalkyl, phenyl which may carry from one to three of the following groups: $C_1$–$C_4$-alkyl, $C_1$–$C_4$-alkoxy, $C_1$–$C_4$-haloalkyl, $C_1$–$C_4$-haloalkoxyl $C_2$–$C_5$-alkoxycarbonyl, halogen, nitro or cyano; one equivalent of a cation from the group consisting of the alkali or alkaline earth metals, manganese, copper, iron, ammonium and substituted ammonium, or a radical —N=$CR^8R^9$;

$R^8$ and $R^9$ independently of one another are each hydrogen, $C_1$–$C_4$-alkyl or $C_3$–$C_6$-cycloalkyl or together may form a methylene chain having 4 to 7 members, $R^6$ and $R^7$ are each hydrogen or $C_1$–$C_6$-alkyl or together may form a methylene chain having 4 or 5 members, with the proviso that X and Z in formula Ia are not simultaneously C—$R^4$, where $R^4$ is halogen, or independently of one another C—$R^4$, where $R^4$ is halogen or hydroxyl, when Y is N, and that X in formula Ia is not C—$R^4$, where $R^4$ is phenyl, when Y is N; with the further proviso that if Z is nitrogen and $R^1$ is a substituted or unsubstituted cycloalkyl group, W is a group C—$R^4$ wherein $R^4$ does not stand for hydrogen, halogen, hydroxy or methyl, and salts thereof which can be used in agriculture are novel.

The pyridine derivatives Ia, Ib and Ic or I′a, I′b and I′c may form addition salts, for example with inorganic and organic acids or with alkyl halides, or, if one of the substituents has acidic properties, said derivatives can be reacted with inorganic and organic bases to form salts. The present invention also relates to the corresponding salts.

Pyridine derivatives which are preferred as herbicidal active ingredients are those of the formulae I′b and I′c where $R^2$ is hydrogen.

Further preferred pyridine derivatives of the formulae I′b and I′c are those in which one of the ring members W, X, Y and Z is N and the others are each C—$R^4$, $R^1$ is $C_3$–$C_6$-alkyl, $C_3$–$C_6$-alkenyl, $C_3$–$C_8$-alkynyl or $C_3$–$C_8$-cycloalkyl, $R^2$ is hydrogen, $R^3$ is a radical —CO—A—$R^5$ and $R^4$ is hydrogen, halogen, nitro, cyano, $C_1$–$C_4$-alkyl, $C_1$–$C_4$-alkoxy, $C_1$–$C_4$-alkylthio, $C_1$–$C_4$-alkylsulfonyl, $C_1$–$C_4$-haloalkyl, $C_1$–$C_4$-haloalkoxy or $C_1$–$C_4$-haloalkylthio. In these compounds, $R^5$ is preferably hydrogen, $C_1$–$C_4$-alkyl, phenyl which is unsubstituted or substituted by $C_1$–$C_4$-alkyl, $C_1$–$C_4$-haloalkyl, $C_1$–$C_4$-alkoxy, $C_1$–$C_4$-alkylthio or halogen, or a radical —N=$CR^8R^9$, where $R^8$ and $R^9$ are each preferably $C_1$–$C_4$-alkyl. A is preferably oxygen; the $C_1$–$C_4$-haloalkyl radical $R^4$ may be substituted by one to five, preferably 3, halogen atoms.

The pyridine derivatives of the formulae Ia, Ib and Ic can be prepared by various methods:

1. The compounds Id and Ie are converted into the pyridine derivatives of the formula Ia by dehydration with water-eliminating agents, for example acetic anhydride or inorganic acid halides. The reaction is advantageously carried out by a procedure in which the carboxamides in an inert organic solvent are initially taken and about molar amounts of a water-eliminating agent, if necessary likewise dissolved in an inert solvent, are added dropwise. The mixture can be worked up in a conventional manner, for example by hydrolysis with water and filtration of the product under suction or by extraction of the product with an organic solvent and evaporation of the organic solvent:

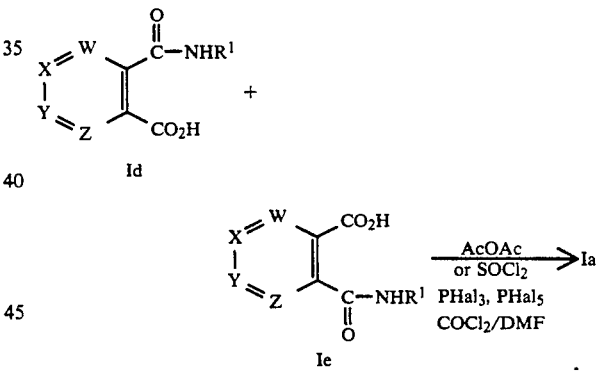

Advantageously, solvents such as halohydrocarbons, e.g. tetrachloroethane, methylene chloride, chloroform, dichloroethane, chlorobenzene and 1,2-dichlorobenzene, ethers, e.g. diethyl ether, methyl tert-butyl ether, dimethoxyethane, diethylene glycol diethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, e.g. benzene, toluene, xylene, pyridine and quinoline, ketones, e.g. acetone and methyl ethyl ketone, and corresponding mixtures are used for these reactions.

The reaction can be carried out at from −10° C. to the reflux temperature of the particular solvent, preferably from 0° to 150° C.

The molar ratios in which the required starting compounds are reacted with one another are in general from 0.9:1 to 5:1 for the ratio of water-eliminating agent to acid amide.

The concentration of the educts in the solvent (mixture) is in general from 0.1 to 5, preferably from 0.2 to 2, mol/l.

2. A process for the preparation of compounds of the formulae Ib and Ic in which $R^3$ is a radical —CO—A—$R^5$, A is oxygen and $R^5$ is hydrogen, is based on the reaction of a substituted pyridinedicarboxylic anhydride with an amine.

The reaction is advantageously carried out by a procedure in which the anhydride II in an inert solvent is initially taken and about molar amounts of an amine III, if necessary likewise dissolved in an inert solvent, are added dropwise. After the end of the reaction, the reaction product is filtered off under suction or is isolated by evaporating the solvent used, the amides Ib or their isomers Ic being obtained.

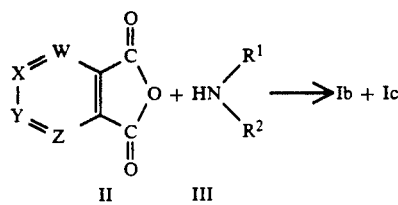

The isomer distribution is essentially determined by the position of the heteroatom. For example, Z=N leads to preferential formation of Ic whereas the formation of Ib takes place preferentially in the case of Y=N.

Advantageously, solvents such as halohydrocarbons, e.g. tetrachloroethane, methylene chloride, chloroform, chlorobenzene and 1,2-dichlorobenzene, ethers, e.g. diethyl ether, methyl tert-butyl ether, dimethoxyethane, diethylene glycol dimethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, e.g. benzene, toluene, xylene, pyridine and quinoline, ketones, e.g. acetone and methyl ethyl ketone, and corresponding mixtures are used for these reactions.

The reaction can be carried out at from −10° C. to the reflux temperature of the particular solvent or solvent mixture, preferably from −20° to 120° C.

The molar ratios in which the required starting compounds are reacted with one another are from 0.9:1 to 3:1 for the ratio of amine III to anhydride II. The concentration of the educts in the solvent is from 0.1 to 5, preferably from 0.2 to 2, mol/l.

The pyridinedicarboxylic acids or anhydrides required as starting materials for this process are commercially available or known from the literature or can be prepared by conventional methods. An overview appears in Beilstein H 22, 150–160, E I 531–536, E II 104–111, H 27 261, E I 319, E II 299, R. C. Elderfield, Heterocyclic Compounds, Vol. I, Chapter 8, J. Wiley and Sons, N.Y., and E. Klingberg, Pyridine and its Derivatives, Part 3, Chapter X, in The Chemistry of Heterocyclic Compounds, 1962, Interscience Publishers, and in EP-A-299 362.

3. A process for the synthesis of compounds of the formulae Ib and Ic, in which $R^3$ is a radical —CO—A—$R^5$, A is oxygen and $R^5$ is hydrogen or $C_1$-$C_6$-alkyl which is unsubstituted or substituted by one to five halogen atoms or one to five hydroxyl groups and/or one of the radicals $C_1$-$C_4$-alkoxy, $C_1$-$C_4$-alkoxy-$C_2$-$C_4$-alkoxy, cyano or $C_1$-$C_3$-alkylthio, comprises reacting a pyridinedicarboxylic mono- or diester IV with an amine III.

Particularly suitable mono- or dialkyl esters IV are lower alkyl esters, preferably dimethyl esters or diethyl esters. The reaction is carried out by a method in which a dicarboxylic mono- or dialkyl ester IV is treated with about one equivalent of a primary or secondary amine III at from 0° to 130° C., preferably from 50° to 100° C., in an organic solvent. After the reaction is complete, the mixture is cooled and the product is filtered off under suction or the solution is evaporated down. The resulting products of the formulae Ib and Ic can be further purified by conventional standard methods, such as recrystallization or chromatography.

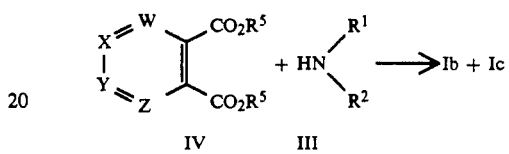

The isomer distribution is essentially determined by the position of the heteroatom. For example, in the case of a dialkyl ester, Z=N leads to the preferential formation of Ic whereas the formation of Ib takes place preferentially when Y=N. In the case of a monoalkyl ester IV, the particular ester radical is displaced regardless of the position of the heteroatom.

Ethers, e.g. diethyl ether, methyl tert-butyl ether, dimethoxyethane, diethylene glycol dimethyl ether, tetrahydrofuran and dioxane, aromatics, e.g. benzene, toluene, xylene and mesitylene, alcohols, e.g. methanol, ethanol, n-propanol, isopropanol and tert-butanol, and corresponding mixtures are used as solvents for these reactions.

The molar ratio in which the mono- or diester IV and the amine III are used is from 0.9:1 to 2:1, preferably from 1:1 to 1:1.2.

The concentration of the educts in the solvent (mixture) is in general from 0.1 to 5, preferably from 0.2 to 2, mol/l.

4. Compounds of the formula Ia may also be prepared by reacting a monoalkyl pyridinedicarboxylate V with a halogenating agent and then reacting the product with an amine III.

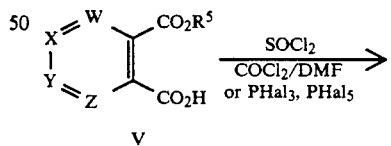

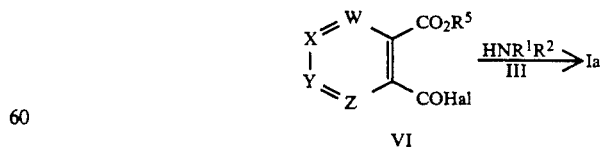

The reaction is carried out by a method in which a half ester V is converted in a conventional manner with an inorganic acid halide, such as thionyl chloride, phosgene, phosphorus trichloride, phosphorus tribromide or phosphorus pentachloride, preferably thionyl chloride, into the acid halide VI.

Advantageously, the inorganic acid halide is used in an amount of from 1 to 5, preferably from 1 to 2, molar equivalents, based on carboxylic acid V used.

It is also possible to carry out the reaction without a solvent or in the presence of an inert inorganic solvent; halohydrocarbons, e.g. tetrachloroethane, methylene chloride, chloroform, dichloroethane, chlorobenzene and 1,2-dichlorobenzene, and aromatics, e.g. benzene, toluene and xylene, are advantageously used. The reaction is carried out at from 0° C. to the boiling point of the inorganic acid halide or of the solvent used, preferably at from 20° to 120° C.

In some cases, the addition of a catalyst, such as dimethylformamide or 4-dimethylaminopyridine, may be advantageous. The concentration of the catalyst is from 0.3 to 20 mol %, based on carboxylic acid V used.

The reaction is particularly preferably carried out without a solvent, in thionyl chloride as the inorganic acid halide, at from 60° to 90° C., in the presence of from 1 to 10 mol % of dimethylformamide as the catalyst.

The conversion of the carbonyl halides VI into the pyridine derivatives Ia is carried out by a procedure in which the carbonyl halide, in an inert organic solvent, such as dichloromethane or an ether, e.g. diethyl ether or methyl tert-butyl ether, is reacted with the amine III, likewise dissolved in an inorganic solvent. The amine is advantageously used in from 2 to 5 times the molar amount, in order to bind the hydrogen halide formed. It is also possible to carry out the reaction in the presence of an auxiliary base, for example a tertiary amine (triethylamine). In this case, from 1 to 1.5 molar equivalents of amine are sufficient. The reaction temperature may be from 0° to 50° C., preferably from 0° to 20° C. The reaction is generally complete after from 1 to 12 hours. The mixture can be worked up in a conventional manner, for example by hydrolysis with water and extraction of the product Ia with an organic solvent and evaporation of the organic solvent. The product of the formula Id can be purified by recrystallization or chromatography.

5. A process for the preparation of compounds Ib in which $R^3$ is formyl or a radical —CO—A—$R^5$, where A is oxygen and $R^5$ is hydrogen, is based on the reaction of a pyridinecarbonyl halide VII with an amine III. Preferred carbonyl halides are the chlorides.

In an advantageous procedure, the carbonyl halide VII, in an inert organic solvent, such as dichloromethane or an ether, e.g. diethyl ether or methyl tert-butyl ether, is reacted with an amine III, likewise dissolved in an organic solvent. The amine is advantageously used in from 2 to 5 times, preferably from 2 to 3 times, the molar amount in order to bind the hydrogen halide formed. It is also possible to carry out the reaction in the presence of an auxiliary base, for example a tertiary amine (triethylamine). In this case, from 1 to 1.5 molar equivalents of amine are sufficient. The reaction temperature may be from 0° to 50° C., preferably from 0° to 20° C. The reaction is complete in general after from 1 to 12 hours. The mixture can be worked up in a conventional manner, for example by hydrolysis with water and extraction of the product VIII with an organic solvent and evaporation of the organic solvent.

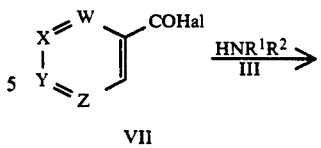

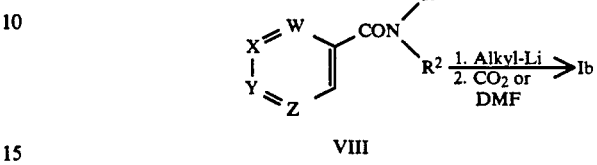

The pyridinedicarboxylic acid semi-amides of the formula Ib are obtained from the pyridineamides VIII by reaction with alkyllithium, preferably with the addition of a solvent which is inert under the reaction conditions, such as diethyl ether, methyl tert-butyl ether, dimethoxyethane, diethylene glycol dimethyl ether, dioxane or tetrahydrofuran. As a rule, the reaction is carried out under a nitrogen atmosphere at from −80° to 30° C. In this process, the alkyllithium compound is generally used in from 2 to 3 times the molar amount, based on amide of the formula VIII used. After the reaction is complete, the mixture is treated with carbon dioxide, preferably in an inert solvent, such as diethyl ether or, for example, tetrahydrofuran, the desired products of the formula Ib, where $R^3$ is carboxyl, being obtained.

Suitable alkyllithium compounds are methyllithium, n-butyllithium, sec-butyllithium and tert-butyllithium. In this process, the organometallic base is used in from 2 to 4 times, preferably from 2 to 2.5 times, the molar amount, based on amide VIII employed.

Pyridinecarboxamides of the formula Ib, in which $R^3$ is formyl, can also be obtained by the same process if dimethylformamide is used instead of carbon dioxide. Substituted pyridinecarboxamides or formylpyridinecarboxamides of the formula Ib are obtained after working up in a conventional manner. The concentration of the educts in the solvent is in general from 0.1 to 5, preferably from 0.2 to 2, mol/l.

6. A further process for the preparation of the compounds Ib comprises treating a semi-amide of the formula If with an alcohol of the formula IX in the presence of a strong mineral acid, e.g. hydrochloric acid or sulfuric acid.

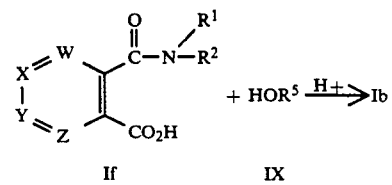

The process leads to compounds Ib in which $R^3$ is a radical —CO—A—$R^5$, A is oxygen and $R^5$ is $C_1$-$C_6$-alkyl which may be substituted by one to five halogen atoms or one to five hydroxyl groups and/or one of the following radicals: $C_1$-$C_4$-alkoxy, $C_1$-$C_4$-alkoxy-$C_2$-$C_4$-alkoxy, cyano or $C_1$-$C_3$-alkylthio;

benzyl which may carry from one to three of the following groups: $C_1$-$C_3$-alkyl, $C_1$-$C_3$-alkoxy, $C_1$-$C_3$-haloalkyl, halogen, nitro or cyano;

$C_3$-$C_8$-cycloalkyl;

phenyl which may carry from one to three of the following groups: $C_1$-$C_4$-alkyl, $C_1$-$C_4$-alkoxy, $C_1$-$C_4$-haloalkyl, $C_1$-$C_4$-haloalkoxyl, $C_2$-$C_5$-alkoxycarbonyl, halogen, nitro or cyano;

a radical —N=$CR^8R^9$, where $R^8$ and $R^9$ independently of one another are each hydrogen, $C_1$-$C_4$-alkyl or $C_3$-$C_6$-cycloalkyl or together may form a methylene chain having from 4 to 7 members.

As a rule, the alcohol is used in excess, for example from 2 to 50 moles per mole of amide If. However, it is also possible to use an inert solvent, such as methylene chloride, dichloroethane, chlorobenzene or 1,2-dichlorobenzene, an ether, e.g. diethyl ether, methyl tert-butyl ether, diethylene glycol dimethyl ether, tetrahydrofuran or dioxane, or corresponding mixtures.

The reaction can be carried out at from 0° to 100° C., preferably from 20° to 60° C.

7. A further process for the preparation of the compounds of formula Ib comprises reacting an acid If with an alcohol or thiol X in the presence of a dehydrating agent (e.g. dicyclohexylcarbodiimide (DCC)) at from −20° to 50° C., preferably from 0° to 30° C. As a rule, the starting materials are reacted in roughly stoichiometric amounts. The reaction is preferably carried out in the presence of one of the abovementioned inert solvents, e.g. tetrahydrofuran, dichloromethane or toluene.

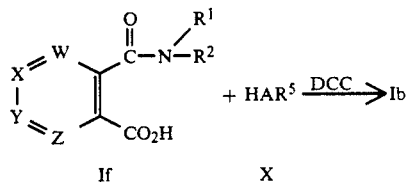

A is oxygen or sulfur and $R^5$ has the meanings stated for process 6.

The molar ratios in which the required starting compounds are reacted with one another are in general from 0.9:1 to 2:1 for the ratio of carboxylic acid If to alcohol or thiol and from 1:1 to 1:3 for the ratio of carboxylic acid If to dehydrating agent.

The concentration of the educts in the solvent is in general from 0.1 to 5, preferably from 0.2 to 2, mol/l.

8. A further process for the preparation of the compounds of the formula Ib comprises reacting a pyridine derivative Ia with an alcohol in the presence of an organic base and of an inert solvent, for example in one of the abovementioned hydrocarbons or an alcohol at from 0° to 80° C., preferably from 20° to 50° C. Examples of suitable organic bases are triethylamine, tri-n-butylamine, pyridine, N,N-dimethylaniline and N,N-dimethylcyclohexylamine.

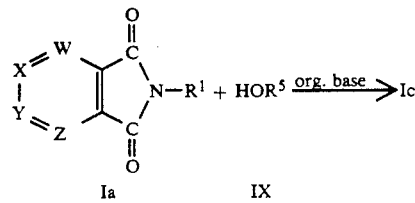

The novel substituent is preferentially introduced meta to the heteroatom. Compounds Ic in which $R^2$ is hydrogen, $R^3$ is a radical —CO—A—$R^5$, A is oxygen and $R^5$ has the meanings stated for formula Ic can be prepared in this manner.

The molar ratios in which the required starting compounds are reacted with one another are in general from 0.9:1 to 200:1 for the ratio of alcohol IX to pyridine derivative Ia, depending on whether the alcohol is used directly as a solvent, and from 0.9:1 to 2:1 for the ratio of the base to the pyridine derivative Ia.

The concentration of the educts in the solvent is in general from 0.1 to 5, preferably from 0.2 to 2, mol/l.

9. A process for the preparation of compounds of the formulae Ib and Ic in which $R^2$ is hydrogen and $R^3$ is a radical —CO—$NR^6R^7$ comprises reacting a pyridine derivative Ia with an amine XI in the presence of one of the above-mentioned inert solvents, for example an ether or an alcohol, at from 0° to 80° C., preferably from 10° to 40° C. The weaker basic amine is preferentially introduced meta to the heteroatom. Isomeric compounds can be separated in a conventional manner, for example by chromatography.

The molar ratios in which the required starting compounds are reacted with one another are in general from 0.9:1 to 20:1 for the ratio of amine XI to pyridine derivative Ia. The concentration of the educts in the solvent is in general from 0.1 to 5, preferably from 0.2 to 2, mol/l.

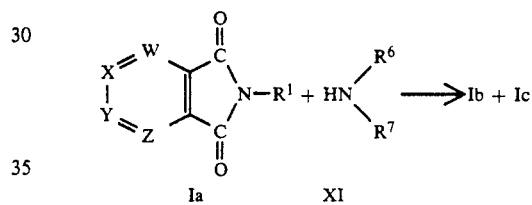

10. Compounds of the formula Ic in which $R^3$ is a radical —CO—A—$R^5$ and $R^5$ is one equivalent of a cation are obtained by reacting a pyridine derivative Ic, where $R^3$ is a radical —CO—A—R5 and $R^5$ hydrogen, with one equivalent of the corresponding salt-forming cation. If this is an inorganic cation, e.g. sodium, potassium or calcium, the acid Ic is advantageously dissolved or suspended in water or in a lower alcohol or in a mixture of these, and one equivalent of the salt-forming cation is added. The salt-forming cation can be used, for example, in the form of its hydroxide, carbonate or bicarbonate, preferably in the form of its hydroxide. The reaction is generally complete after a few minutes and the reaction mixture can be worked up in a conventional manner, for example by precipitation and filtration under suction or by evaporating down the solution. For the preparation of compounds Ic in which $R^5$ is ammonium or organic ammonium, the acid Ic is dissolved or suspended in an organic solvent, e.g. diethyl ether, tetrahydrofuran or dioxane, and the mixture is treated with one equivalent of ammonia, an amine or a tetraalkylammonium hydroxide.

Examples of amines which may be used are methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butyldmine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-buten-2-ylamine, n-penten-2-ylamine, 2,3-dimethylbuten-2-ylamine, dibuten-2-ylamine, n-hexen-2-ylamine, propenylenediamine, tallow amine, cyclopentylamine, cyclohexylamine, dicyclohexylamine, piperidine, morpholine and pyrrolidine.

In the case of the tetraalkylammonium hydroxides, it is possible to use, for example, tetramethyl-, tetraethyl- or trimethylbenzylammonium hydroxide. As a rule, the ammonium salt or organic ammonium salt is precipitated from the solution and can be isolated by conventional methods. Alternatively, the salt of the formula Ic can also be obtained by evaporating down the solvent.

The reaction can be carried out at from −10° to 80° C., preferably from 20° to 40° C.

11. A process for the preparation of the compounds of the formula Ia in which one of the ring members X, Y and Z is N and another is C—R⁴ where R⁴ is halogen comprises first reacting a pyridine derivative of the formula Ia where one of the ring members Y, X and Z is N with an oxidizing agent, for example m-chloroperbenzoic acid or hydrogen peroxide, in an inert organic solvent, for example one of the abovementioned halohydrocarbons, such as methylene chloride, or an alkanecarboxylic acid, such as glacial acetic acid, to give the N-oxide at from 0° to 100° C., preferably from 20° to 60° C., and then reacting said N-oxide with a phosphorus oxyhalide, for example phosphorus oxychloride, to give the halogen compound at from 80° to 120° C.

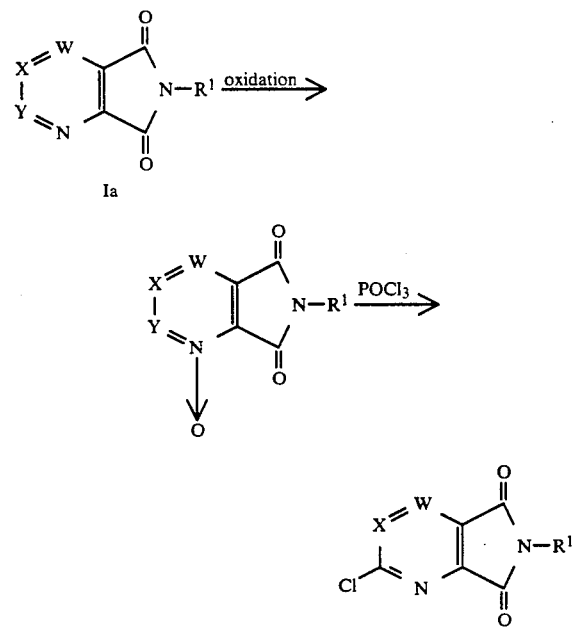

The molar ratios in which the required starting compounds are reacted with one another are in general from 1:0.9 to 1:1.5 for the ratio of imide Ia to the oxidizing agent. In the subsequent halogenation step, an inert solvent, such as chlorobenzene, may be used, but the reaction is advantageously carried out directly in excess phosphorus oxyhalide as a reaction medium.

The concentration of the educts in the solvent (mixture) is in general from 0.1 to 5, preferably from 0.2 to 2, mol/l.

The individual process steps are known from the literature or can be carried out by methods generally known from the literature (J. Org. Chem. 19 (1954), 1633).

12. A process for the preparation of the compounds of the formula Ia comprises reacting a haloimide of the formula Ia where one or more of the ring members W, X, Y or Z are C—R⁴ in which R⁴ is halogen with the salt of an alcohol or of a thiol XII in the presence of excess alcohol or of an inert organic solvent.

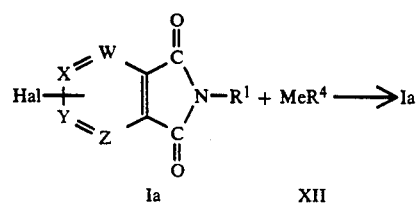

In formulae Ia and XII, $R^4$ is $C_1$–$C_4$-alkoxy or $C_1$–$C_4$-alkylthio, each of which may be monosubstituted to trisubstituted by halogen, $C_3$- or $C_4$-alkenyloxy, $C_3$- or $C_4$-alkynyloxy or phenoxy or phenylthio, each of which may be monosubstituted to trisubstituted by $C_1$–$C_4$-alkyl, $C_1$–$C_4$-haloalkyl, $C_1$–$C_4$-alkylthio, $C_1$–$C_4$-haloalkylthio, halogen, cyano or nitro.

Me is an alkali metal or alkaline earth metal ion, for example lithium, sodium, potassium, magnesium or calcium.

Solvents such as halohydrocarbons, e.g. tetrachloroethane, methylene chloride, chloroform, dichloroethane, chlorobenzene and 1,2-dichlorobenzene, ethers, e.g. diethyl ether, methyl tert-butyl ether, dimethoxyethane, diethylene glycol dimethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, e.g. benzene, toluene, xylene, pyridine and quinoline, ketones, e.g. acetone and methyl ethyl ketone, alcohols, e.g. methanol, ethanol, isopropanol and tertbutanol, and corresponding mixtures are advantageously used for these reactions.

The reaction can be carried out at from 20° C. to the reflux temperature of the particular solvent or solvent mixture, preferably at from 40° to 150° C.

The bases used are hydrides and alkoxides of alkali metal and alkaline earth metal cations, in particular NaH, KH, CaH₂, LiH and potassium butoxide. It is sometimes also useful to use combinations of the abovementioned bases.

The molar ratios in which the required starting compounds are reacted with one another are in general from 0.9:1 to 1.5:1 for the ratio of alcohol or thiol to halogenated imide Ia and from 1:1 to 1:3 for the ratio of alcohol or thiol to the effective base.

The concentrations of the educts in the solvent are in general from 0.1 to 5, preferably from 0.2 to 2, mol/l.

The process can be carried out by methods generally known from the literature (U.S. Pat. No. 4,647,301).

13. Pyridine derivatives Ia in which $R^4$ in $C—R^4$ is $C_1$-$C_4$-haloalkyl, $C_1$-$C_4$-haloalkoxy or $C_1$-$C_4$-haloalkylmercapto can be obtained in a first step by halogenation of a pyridinedicarboxylic anhydride of the formula II, where $R^4$ is $C_1$-$C_4$-alkyl, $C_1$-$C_4$-alkoxy or $C_1$-$C_4$-alkylthio, at from 60° to 150° C., preferably from 80° to 130° C., in the presence of one of the abovementioned inert aromatic halohydrocarbons, e.g. chlorobenzene, and in the presence or absence of a free radical initiator, such as $\alpha,\alpha'$-azoisobutyronitrile. This is followed, in a second step, by halogen exchange by antimony(III) fluoride in the presence or absence of a catalytic amount of antimony(V) chloride. For this purpose, a mixture of anhydride II' and antimony(III) fluoride is heated to about 80° C., if necessary the catalyst is then added a little at a time and the mixture is heated further until the exothermic reaction continues by itself, preferably at from 110° to 140° C. After stirring has been carried out for from 20 to 60 minutes, the reaction solution is taken up in a chlorohydrocarbon, decomposition is effected in a conventional manner with hydrochloric acid and the organic phase is worked up. The anhydride II'' thus obtained is then converted into the corresponding imide Ia by processes 1 and 2.

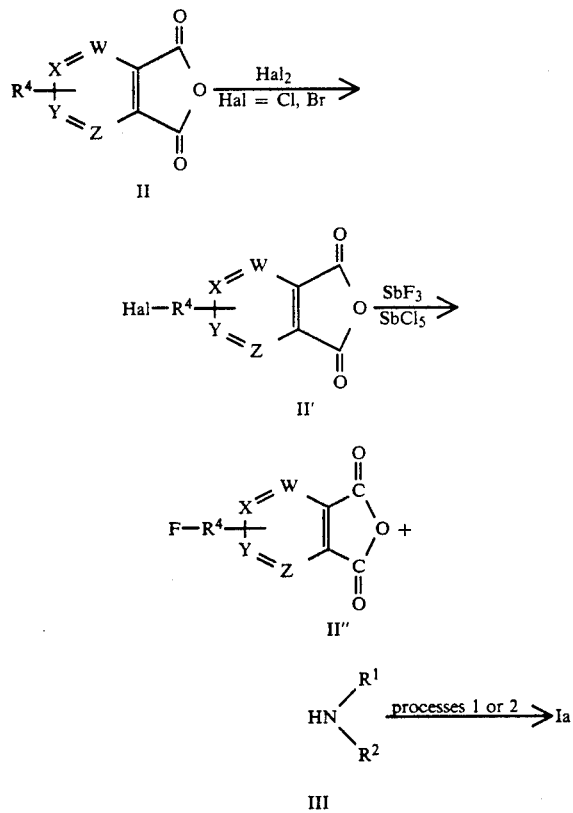

The molar ratios in which the required starting compounds are reacted with one another are in general from 0.9 to 3 moles of halogen for the C—H bond to be halogenated in II and from 0.25 to 0.33 mole of antimony-(III) fluoride for the halogen equivalent to be exchanged in II.

The concentration of the educts in the solvent (mixture) is in general from 0.1 to 5, preferably from 0.2 to 2, mol/l.

The process can be carried out by methods generally known from the literature (DE-A-2 914 915), and the degree of fluorination can be controlled by the amount of fluorinating agent.

14. Compounds of the formula Ia in which $R^4$ in $C—R^4$ is $C_1$-$C_4$-haloalkyl are obtained if amides I''a substituted $\alpha$ to the heteroatoms by $C_1$-$C_6$-alkyl are reacted, in a first step, with an oxidizing agent, for example m-chloroperbenzoic acid or hydrogen peroxide, in an inert organic solvent, for example one of the abovementioned halohydrocarbons, such as methylene chloride or chlorobenzene, or an alkanecarboxylic acid, such as glacial acetic acid, or an aromatic, such as toluene, to give the corresponding N-oxides at from 0° to 100° C., preferably from 20° to 60° C., and the latter are then converted into the halogen compounds I'''a with a phosphorus oxyhalide, for example phosphorus oxychloride,, at from 80° to 120° C. For the pyridine-2,3-dicarboximides, the reaction takes place in accordance with the following scheme:

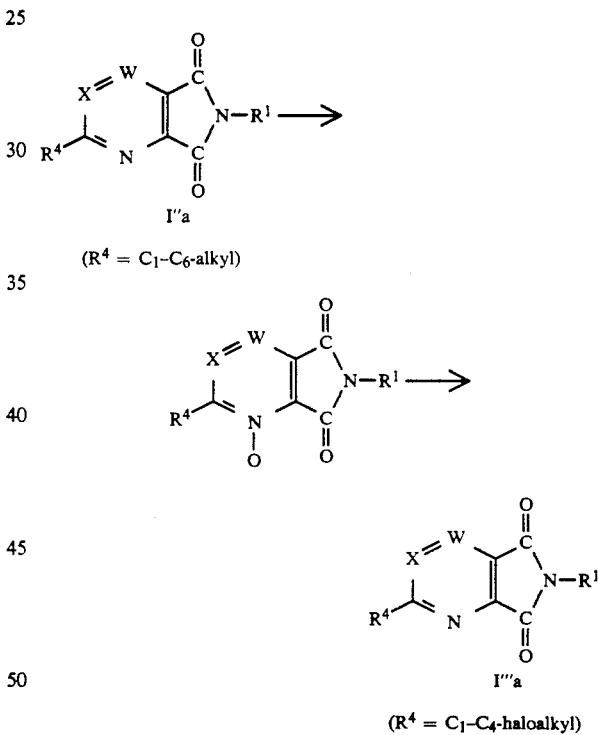

The molar ratios and the procedure are based on the reaction conditions of process 11. The individual process steps can be carried out by methods generally known from the literature.

In view of the intended use of the compounds II a, I'b and I'c, for example, the following radicals are suitable substituents:

W, X, Y and Z are each $C—R^4$, nitrogen or N-oxide; $R^1$ is hydrogen, hydroxy, $C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy; $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, propyl, 1-methylethyl or 1,1-dimethylethyl, which may carry from one to three of the following groups:

$C_1$-$C_4$-alkoxy as stated above, in particular methoxy or ethoxy;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1, 1, 2-trifluoroethoxy or pentafluoroethoxy, in particular trifluoromethoxy or pentafluoroethoxy;

alkylthio, such as methylthio, ethylthio, propylthio, 1-methylethylthio, n-butylthio, 1-methylpropylthio, 2-methylpropylthio or 1,1-dimethylethylthio, in particular methylthio or ethylthio;

haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio;

dialkylamino, such as dimethylamino, diethylamino, dipropylamino, diisopropylamino, dibutylamino or methylethylamino, in particular dimethylamino or methylethylamino;

cyano;

halogen, such as fluorine, chlorine, bromine or iodine, in particular fluorine or chlorine;

cycloalkyl, such as cyclopropyl, cyclobutyl, cyclopentyl, cyclohexyl, cycloheptyl or cyclooctyl, in particular cyclopropyl, cyclopentyl or cyclohexyl, or phenyl which may be substituted by halogen, cyano, nitro, alkyl as stated above, in particular methyl or ethyl, haloalkyl as stated above, in particular trifluoromethoxy;

alkoxy, as stated above, in particular methoxy or ethoxy, haloalkoxy as stated above, in particular trifluoromethoxy, or haloalkylthio;

$C_3$-$C_8$-cycloalkyl as stated above, in particular cyclopropyl, cyclobutyl, cyclopentyl or cyclohexyl, which may carry from one to three of the following groups: alkyl as stated above, in particular methyl, ethyl or isopropyl, haloalkyl as stated above, in particular trifluoromethyl, alkoxy as stated above, in particular methoxy or ethoxy, haloalkoxy as stated above, in particular trifluoromethoxy, halogen as stated above, in particular fluorine or chlorine, nitro or cyano;

$C_3$-$C_6$-alkenyl, such as 2-propenyl, 2-methylethenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl,2-methyl-3-butenyl,3-methyl-3-butenyl, 1,1-dimethyl-2-propenyl, 1,2-dimethyl-2-propenyl, 1-ethyl-2-propenyl, 1-hexenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1, 1-dimethyl-2-butenyl, 1, 1-dimethyl-3-butenyl, 1,2-dimethyl-2-butenyl, 1,2-dimethyl-3-butenyl, 1,3-dimethyl-2-butenyl, 1, 3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2 -ethyl - 3 -butenyl, 1,1,2-trimethyl-2 -propenyl, 1-ethyl-1-methyl-2-pentenyl or ethyl-2-methyl-2-pentenyl, in particular ethenyl, 2-propenyl, 1-methylethenyl, 2-butenyl, 3-butenyl, 1-methylpropyl, 1-methyl-2-propenyl, 2-methyl-2-propenyl, which may be monosubstituted to trisubstituted by halogen as stated above, in particular fluorine or chlorine, and/or monosubstituted by phenyl, where the phenyl radical in turn may carry from one to three of the following groups: alkyl as stated above, in particular trifluoromethyl or chlorodifluoromethyl, alkoxy as stated above, in particular methoxy or ethoxy, haloalkoxy as stated above, in particular trifluoromethoxy, trichloromethoxyorpentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano or nitro;

$C_3$-$C_6$-alkynyl, such as propargyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 3-methyl-1-butynyl, 1, 1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1, 1-dimethyl-3-butynyl, 1, 2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 1-methyl-2-propynyl or 1,1-dimethyl-2-propynyl, which may be monosubstituted to trisubstituted by halogen as stated above, in particular fluorine or chlorine, and/or monosubstituted by phenyl, where the phenyl radical in turn may carry f rom one to three of the following groups: alkyl as stated above, in particular methyl, ethyl or 1-methylethyl, haloalkyl as stated above, in particular trifluoromethyl or chlorodifluoromethyl, alkoxy as stated above, in particular methoxy or ethoxy, haloalkoxy as stated above, in particular trifluoromethoxy, trichloromethoxy or pentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano or nitro;

$C_1$-$C_4$-dialkylamino as stated above, in particular dimethylamino, diethylamino or diisopropylamino;

a 5-membered or 6-membered saturated or aromatic heterocyclic radical containing one or two hetero atoms selected from the group consisting of oxygen, sulfur and nitrogen, such as tetrahydrofuryl, tetrahydropyranyl, furyl, thienyl, thiazolyl, pyrazolyl, pyrrolyl, pyridyl, morpholino, piperidino or pyrimidyl, for example 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furyl, 3-furyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl or 4-pyridyl, which may carry from one to three of the following substituents: alkyl as stated above, in particular methyl or ethyl, or halogen as stated above, in particular fluorine or chlorine;

phenyl which may carry from one to four of the following groups: alkyl as stated above, in particular methyl, ethyl or isopropyl, haloalkyl as stated above, in particular trifluoromethyl or chlorodifluoromethyl, alkoxy as stated above, in particular methoxy or ethoxy, haloalkoxy as stated above, in particular trifluoromethoxy, trichloromethoxy or pentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano, nitro, formyl, $C_1$-$C_4$-alkanoyl, such as acetyl, propionyl or butyryl, in particular acetyl, haloalkanoyl, such as trifluoroacetyl, trichloroacetyl, or pentafluoropropionyl, in particular trifluoroacetyl, or alkoxycarbonyl as stated under $R^1$, in particular methoxycarbonyl;

naphthyl which may be monosubstituted to trisubstituted by alkyl as stated under $R^1$, in particular methyl or ethyl, or halogen as stated under $R^1$, in particular fluorine or chlorine;

$R^2$ is hydrogen;

$C_1$-$C_6$-alkyl as stated under $R^1$, in particular methyl, ethyl, 1-methylethyl, which may carry from one to three of the following substituents: hydroxyl, halogen as stated under $R^1$, in particular fluorine or chlorine, alkoxy as stated under $R^1$, in particular methoxy or ethoxy, alkylthio as stated under $R^1$, in particular methylthio or ethylthio, or dialkylamino as stated under $R^5$, in particular dimethylamino;

$C_3$-$C_8$-cycloalkyl as stated under $R^1$, in particular cyclopropyl, cyclobutyl, cyclopentyl or cyclohexyl, which may be monosubstituted to trisubstituted by alkyl as stated under $R^1$, in particular methyl, ethyl or isopropyl, halogen as stated under $R^1$, in particular fluorine or chlorine, or haloalkyl as stated under $R^1$, in particular trifluoromethyl, or $R^1$ and $R^2$ together form a $C_2$-$C_6$-methylene chain which may be interrupted by oxygen, sulfur or N-methyl, such as $-(CH_2)_3-$, $-(CH_2)_4-$, $-(CH_2)_5-$, $-(CH_2)_6-$, $-CH_2-O-CH_2-$, $-CH_2-CH_2-O-CH_2-CH_2-$, $-CH_2-S-CH_2-$, $-CH_2-CH_2-S-CH_2-CH_2-$, $-CH_2-CH_2-N(CH_3)-CH_2-CH_2-$, in particular $-(CH_2)_5-$ or $-CH_2-CH_2-O-CH_2-CH_2-$, or the radical of the formula $-(CH_2)_3-CO-$;

$R^3$ is formyl, 4,5-dihydrooxazol-2-yl or a radical $-COAR^5$ or $-CONR^6R^7$;

A is oxygen or sulfur;

$R^5$ is hydrogen;

alkyl as stated for $R^1$, in particular methyl, ethyl, propyl, 1-methylethyl or hexyl, which may carry from one to five halogen atoms as stated under $R^1$, in particular fluorine or chlorine, from one to five hydroxyl groups and/or one of the following radicals: alkoxy as stated under $R^1$, in particular methoxy or ethoxy;

alkoxyalkoxy, such as methoxyethoxy, ethoxyethoxy or propoxyethoxy, in particular methoxyethoxy, cyano, trimethylsilyl, alkylthio as stated under $R^1$, in particular methylthio or ethylthio, alkylamino, such as methylamino, ethylamino, propylamino or 1-methylethylamino, in particular methylamino or ethylamino, dialkylamino, such as dimethylamino, diethylamino, dipropylamino, diisopropylamino or methylethylamino, in particular dimethylamino or methylethylamino, alkylsulfinyl, such as methylsulfinyl, ethylsulfinyl, propylsulfinyl or 1-methylethylsulfinyl, in particular methylsulfinyl or ethylsulfinyl, alkylsulfonyl, such as methylsulfonyl, ethylsulfonyl, propylsulfonyl or 1-methylethylsulfonyl, in particular methylsulfonyl or ethylsulfonyl, carboxyl, alkoxycarbonyl, such as methoxycarbonyl or ethoxycarbonyl, alkoxycarbonylalkoxy, such as methoxycarbonylmethoxy, methoxycarbonylethoxy or ethoxycarbonylethoxy, alkoxycarbonylalkoxycarbonyl, such as methoxycarbonylmethoxycarbonyl, methoxycarbonylethoxycarbonyl or ethoxycarbonylethoxycarbonyl, dialkylaminocarbonyl, such as dimethylaminocarbonyl, diethylaminocarbonyl, dipropylaminocarbonyl, diisopropylaminocarbonyl or methylethylaminocarbonyl, in particular dimethylaminocarbonyl or diethylaminocarbonyl, dialkoxyphosphonyl, such as dimethoxyphosphonyl, diethoxyphosphonyl, dipropoxyphosphonyl or diisopropoxyphosphonyl, in particular dimethoxyphosphonyl or diethoxyphosphonyl, alkaniminoxy, such as 2-propaniminoxy, thienyl, furanyl, tetrahydrofuranyl, N-phthalimido, pyridyl, benzyloxy or benzoyl, where these cyclic radicals may carry from one to three of the following groups: halogen, in particular fluorine or chlorine, alkoxy, in particular methoxy or ethoxy, or alkyl, in particular methyl or ethyl;

benzyl which may carry from one to three of the following groups: nitro, cyano, halogen, in particular fluorine or chlorine, alkyl as stated under $R^1$, in particular methyl or ethyl, alkoxy as stated under $R^1$, in particular methoxy or ethoxy, or haloalkyl as stated in general and in particular under $R^1$;

cycloalkyl as stated under $R^1$, in particular cyclopentyl or cyclohexyl;

phenyl which may carry from one to three of the following groups: alkyl as stated under $R^1$, in particular methyl or ethyl, alkoxy as stated under $R^1$, in particular methoxy or ethoxy, haloalkyl as stated under $R^1$, in particular trifluoromethyl, haloalkoxy as stated under $R^1$, in particular trifluoromethoxy, alkoxycarbonyl as stated above, in particular methoxycarbonyl, halogen as stated under $R^1$, in particular fluorine, chlorine or bromine, nitro or cyano;

$C_3$-$C_8$-alkenyl as stated under $R^1$, in particular 2-propenyl or 2-butenyl, $C_5$- or $C_6$-cycloalkenyl, such as 2-cyclopentenyl or 2-cyclohexenyl, in particular 2-cyclohexenyl, $C_3$-$C_8$-alkynyl as stated under $R^1$, in particular 2-propynyl, where the three last-mentioned groups may carry one of the following radicals: hydroxyl, alkoxy as stated under $R^1$, in particular methoxy or ethoxy, halogen as stated under $R^1$, in particular fluorine or chlorine, phenyl which in turn may carry from one to three of the following groups: alkyl as stated under $R^1$, in particular methyl or ethyl, alkoxy as stated under $R^1$, in particular methoxy or ethoxy, haloalkyl as stated under $R^1$, in particular trifluoromethyl, halogen as stated under $R^1$, in particular fluorine or chlorine, nitro or cyano;

a five-membered or six-membered heterocyclic radical having one or two hetero atoms selected from the group consisting of oxygen, sulfur and nitrogen, as stated under $R^1$, in particular tetrahydrofuranyl or tetrahydropyranyl, or benzotriazolyl;

N-phthalimido, tetrahydrophthalimido, succinimido or maleimido;

one equivalent of a cation from the group consisting of the alkali metal or alkaline earth metals, manganese, copper, iron, ammonium and substituted ammonium, or $-N=CR^8R^9$, where $R^8$ and $R^9$ are each hydrogen, alkyl as stated under $R^2$, in particular methyl, ethyl or isopropyl;

cycloalkyl as stated under $R^1$, in particular cyclopropyl;

phenyl or furyl, or together form a methylene chain having from 4 to 7 members;

$R^6$ is hydrogen, $C_1-C_6$-alkyl as stated under $R^1$, in particular methyl or ethyl, or $C_3-C_8$-cycloalkyl as stated under $R^1$, in particular cyclopropyl;

$R^7$ is hydrogen or $C_1-C_6$-alkyl as stated under $R^1$, in particular methyl, ethyl, propyl, 1-methylethyl or 1,1-dimethylethyl, or $R^6$ and $R^7$ together form a methylene chain having 4 or 5 members;

$R^4$ is hydrogen, halogen as stated under $R^1$, in particular fluorine or chlorine, nitro, cyano, alkyl as stated under $R^1$, in particular methyl, ethyl, propyl, 1-methylethyl or 1,1-dimethylethyl, which may carry from one to five halogen atoms as stated under $R^1$, in particular fluorine or chlorine, and/or one or two of the following radicals: cyano, alkoxy as stated under $R^1$, in particular methoxy, ethoxy, 1-methylethoxy or 1,1-dimethylethoxy, haloalkoxy as stated under $R^1$, in particular difluoromethoxy or trifluoromethoxy, alkylthio as stated under $R^1$, in particular methylthio or ethylthio, haloalkylthio as stated under $R^1$, in particular difluoromethylthio or trifluoromethylthio;

cycloalkyl as stated under $R^1$, in particular cyclopropyl; benzyl which may be monosubstituted to trisubstituted by alkyl of 1 to 4 carbon atoms as stated under $R^1$, in particular methyl, ethyl or 1-methylethyl, haloalkyl as stated under $R^1$, in particular trifluoromethyl or chlorodifluoromethyl, alkoxy as stated under $R^1$, in particular methoxy or ethoxy, haloalkoxy as stated under $R^1$, in particular trifluoromethoxy, trichloromethoxy or pentafluoroethoxy, alkylthio as stated under $R^1$, in particular methylthio or ethylthio, haloalkylthio as stated under $R^1$, in particular difluoromethylthio, trifluoromethylthio or pentafluoromethylthio, halogen as stated under $R^1$, in particular fluorine or chlorine, cyano or nitro;

$C_3-C_8$-cycloalkyl as stated under $R^1$, in particular cyclopropyl, cyclopentyl or cyclohexyl, which may be monosubstituted to trisubstituted by alkyl as stated under $R^1$, in particular methyl or ethyl, or halogen as stated under $R^1$, in particular fluorine or chlorine;

$C_2-C_6$-alkenyl as stated under $R^1$, and 1-ethenyl, 1-propenyl, 1-methyl-1-propenyl, 2-methyl-1-propenyl, 1-pentenyl, 1-methyl-1-butenyl, 2-methyl-1-butenyl, 1-ethyl-1-propenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl, 2,3-dimethyl-1-butenyl, 3,3-dimethyl-1-butenyl, ethyl-1-butenyl, 2-ethyl-1-butenyl or 1-ethyl-2-methyl-1-pentenyl, in particular ethenyl, 1-propenyl, 2-propenyl, 1-methylethenyl, 1-butenyl, 2-butenyl, 3-butenyl, 1-methylpropenyl, 1-methyl-2-propenyl, 2-methyl-1-propenyl or 2-methyl-2-propenyl, which may be monosubstituted to trisubstituted by halogen as stated under $R^1$, in particular fluorine or chlorine, or alkoxy as stated under $R^1$, in particular methoxy or ethoxy, and/or monosubstituted by phenyl, where the phenyl radical in turn may carry from one to three of the following groups: alkyl as stated under $R^1$, in particular methyl, ethyl or 1-methylethyl, haloalkyl as stated under $R^1$, in particular trifluoromethyl or chlorodifluoromethyl, alkoxy as stated under $R^1$, in particular methoxy or ethoxy, haloalkoxy as stated under $R^1$, in particular trifluoromethoxy, trichloromethoxy or pentafluoroethoxy, alkylthio as stated under $R^1$, in particular methylthio or ethylthio, haloalkylthio as stated under $R^1$, in particular difluoromethylthio, trifluoromethylthio or pentafluoromethylthio, halogen as stated under $R^1$, in particular fluorine or chlorine, cyano or nitro;

alkynyl as stated under $R^1$, and ethynyl, 1-propynyl, 1-butynyl, 1-pentynyl, 1-hexynyl, 3-methyl-1-pentynyl or 4-methyl-1-pentynyl, in particular ethynyl, 1-propynyl or propargyl, which may be monosubstituted to trisubstituted by halogen as stated above, in particular fluorine or chlorine, or alkoxy as stated above, in particular methoxy or ethoxy, and/or monosubstituted by phenyl, where the phenyl radical in turn may carry from one to three of the following groups: alkyl as stated above, in particular methyl, ethyl or 1-methylethyl, haloalkyl as stated above, in particular trifluoromethyl or chlorodifluoromethyl, alkoxy as stated above, in particular methoxy or ethoxy, haloalkoxy as stated above, in particular trifluoromethoxy, trichloromethoxy or pentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano or nitro;

$C_1-C_4$-alkoxy as stated under $R^1$, in particular methoxy or ethoxy;

$C_1-C_4$-haloalkoxy as stated above, in particular trifluoromethoxy, trichloromethoxy or pentafluoroethoxy;

$C_2-C_4$-alkenyloxy, such as vinyloxy, 2-propenyloxy, 1-methylethenyloxy or 2-methyl-3-butenyloxy, in particular 2-propenyloxy or 2-methyl-3-butenyloxy;

$C_2-C_4$-alkynyloxy, such as ethynyloxy, 2-propynyloxy, 1-methylethynyloxy or 2-methyl-3-butynyloxy, in particular 2-propynyloxy or 2-methyl-3-butynyloxy;

$C_1$–$C_4$-alkylthio as stated under $R^1$, in particular methylthio or ethylthio;

$C_1$–$C_4$-haloalkylthio as stated under $R^1$, in particular difluoromethylthio, trifluoromethylthio or pentafluoroethylthio;

$C_1$–$C_4$-alkylsulfinyl, such as methylsulfinyl, ethylsulfinyl, n-propylsulfinyl, isopropylsulfinyl, n-butylsulfinyl or tert-butylsulfinyl, in particular methylsulfinyl;

$C_1$–$C_4$-alkylsulfonyl, such as methylsulfonyl, ethylsulfonyl, n-propylsulfonyl, isopropylsulfonyl, n-butylsulfonyl or tert-butylsulfonyl, in particular methylsulfonyl;

$C_1$–$C_4$-haloalkylsulfonyl, such as trifluoromethylsulfonyl, pentafluoroethylsulfonyl or monofluorobutylsulfonyl, in particular trifluoromethylsulfonyl;

phenoxy or phenylthio which may be monosubstituted to trisubstituted by alkyl as stated under $R^1$, in particular methyl, ethyl or isopropyl, haloalkyl as stated under $R^1$, in particular trifluoromethyl or chlorodifluoromethyl, alkoxy as stated above, in particular methoxy or ethoxy, haloalkoxy as stated above, in particular trifluoromethoxy, trichloromethoxy or pentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano or nitro;

a 5-membered or 6-membered saturated or aromatic heterocyclic radical containing one or two hetero atoms selected from the group consisting of oxygen, sulfur and nitrogen, as stated under $R^1$, which may carry one or two of the following substituents: alkyl as stated under $R^1$, in particular methyl, halogen as stated under $R^1$, in particular fluorine or chlorine, alkoxy as stated under $R^1$, in particular methoxy or ethoxy, or alkoxycarbonyl, such as methoxycarbonyl or ethoxycarbonyl, in particular methoxycarbonyl;

phenyl which may carry from one to three of the following groups: alkyl as stated under $R^1$, in particular methyl, ethyl or isopropyl, haloalkyl as stated under $R^1$, in particular trifluoromethyl or chlorodifluoromethyl, alkoxy as stated under $R^1$, in particular methoxy or ethoxy, haloalkoxy as stated under $R^1$, in particular trifluoromethoxy, trichloromethoxy or pentafluoroethoxy, alkylthio as stated under $R^1$, in particular methylthio or ethylthio, haloalkylthio as stated under $R^1$, in particular difluoromethylthio, trifluoromethylthio or pentafluoromethylthio, halogen as stated under $R^1$, in particular fluorine or chlorine, cyano or nitro.

Examples of herbicidal compounds of the formulae I'a, I'b and I'c are shown in the Tables below:

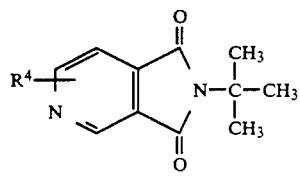

Ia or

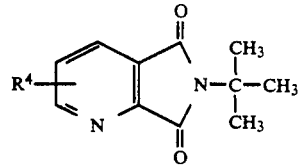

$R^4$ monosubstituted in the 2-, 5- or 6-position, radicals $R^4$ independently of one another disubstituted in the 2,5-, 2,6- or 5,6-position or trisubstituted in the 2,5,6-position or monosubstituted in the 4-, 5- or 6-position or independently of one another disubstituted in the 4,5-, 5,6- or 4,6-position or trisubstituted in the 4,5,6-position

| $R^4$ |
| --- |
| H |
| F |
| Cl |
| Br |
| I |
| Methyl |
| Ethyl |
| n-Propyl |
| Isopropyl |
| n-Butyl |
| Isobutyl |
| sec-Butyl |
| tert-Butyl |
| Cyclopropyl |
| Cyclobutyl |
| Cyclopentyl |
| Cyclohexyl |
| Cycloheptyl |
| Cyclooctyl |
| 1-Methylcyclopropyl |
| Cyclopropylmethyl |
| 1-(Cyclopropyl)-ethyl |
| Dichloromethyl |
| Trichloromethyl |
| Chlorodifluoromethyl |
| Trifluoromethyl |
| Pentafluoroethyl |
| Difluoromethyl |
| Methoxymethyl |
| 1-Methylmethoxymethyl |
| 1-Methyl-2-methoxyethyl |
| 1-Methylethoxymethyl |
| Ethoxymethyl |
| Vinyl |
| Allyl |
| Methallyl |
| Crotyl |
| Propargyl |
| Cinnamyl |
| 1-Methyl-2-propenyl |
| 1-Methyl-2-propynyl |
| Methoxy |
| Ethoxy |
| n-Propoxy |
| Isopropoxy |
| n-Butoxy |
| Isobutoxy |
| sec-Butoxy |
| tert-Butoxy |
| Methylthio |
| Ethylthio |
| Chlorodifluoromethoxy |
| Trifluoromethoxy |
| Chlorodifluoromethylthio |
| Trifluoromethylthio |
| Difluoromethoxy |
| Difluoromethylthio |
| Trichloromethoxy |
| Trichloromethylthio |
| Allyloxy |
| Allylthio |

-continued

| R⁴ |
|---|
| Propargyloxy |
| Propargylthio |
| Cyanomethyl |
| 2-Cyanoethyl |
| 1-Methyl-2-cyanoethyl |
| 1-Methyl-1-cyanoethyl |
| 1,1-Dimethyl-2-cyanoethyl |
| Methylsulfinyl |
| Ethylsulfinyl |
| n-Propylsulfinyl |
| Isopropylsulfinyl |
| Methylsulfonyl |
| Ethylsulfonyl |
| n-Propylsulfonyl |
| Isopropylsulfonyl |
| Trifluoromethylsulfonyl |
| Chloromethyl |
| 2-Chloroethyl |
| 1-Methyl-2-chloroethyl |
| 1-Methyl-1-chloroethyl |
| Nitro |
| Cyano |
| Phenyl |
| 2-F-phenyl |
| 3-F-phenyl |
| 4-F-phenyl |
| 2-Cl-phenyl |
| 3-Cl-phenyl |
| 4-Cl-phenyl |
| 2-CH₃-phenyl |
| 3-CH₃-phenyl |
| 4-CH₃-phenyl |
| 2-CF₃-phenyl |
| 3-CF₃-phenyl |
| 4-CF₃-phenyl |
| 2-OCH₃-phenyl |
| 3-OCH₃-phenyl |
| 4-OCH₃-phenyl |
| 2,4-Dichlorophenyl |
| Phenoxy |
| Phenylthio |
| 2-Cl-phenoxy |
| 3-Cl-phenoxy |
| 4-Cl-phenoxy |
| 2,4-dichlorophenoxy |
| Benzyl |
| 2-Cl-benzyl |
| 3-Cl-benzyl |
| 4-Cl-benzyl |
| 2-Thienyl |
| 3-Thienyl |
| 2-Pyridyl |
| 3-Pyridyl |

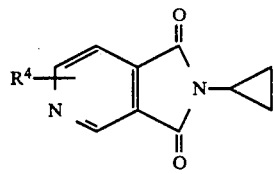

Ia or

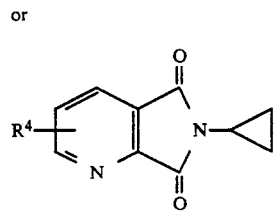

R⁴ monosubstituted in the 2-, 5- or 6-position, radicals R⁴ independently of one another disubstituted in the 2,5-, 2,6- or 5,6-position or trisubstituted in the 2,5,6-position or monosubstituted in the 4-, 5- or 6-position or independently of one another disubstituted in the 4,5-, 5,6- or 4,6-position or trisubstituted in the 4,5,6-position

| R⁴ |
|---|
| H |
| F |
| Cl |
| Br |
| I |
| Methyl |
| Ethyl |
| n-Propyl |
| Isopropyl |
| n-Butyl |
| Isobutyl |
| sec-Butyl |
| tert-Butyl |
| Cyclopropyl |
| Cyclobutyl |
| Cyclopentyl |
| Cyclohexyl |
| Cycloheptyl |
| Cyclooctyl |
| 1-Methylcyclopropyl |
| Cyclopropylmethyl |
| 1-(Cyclopropyl)-ethyl |
| Dichloromethyl |
| Trichloromethyl |
| Chlorodifluoromethyl |
| Trifluoromethyl |
| Pentafluoroethyl |
| Difluoromethyl |
| Methoxymethyl |
| 1-Methylmethoxymethyl |
| 1-Methyl-2-methoxyethyl |
| 1-Methylethoxymethyl |
| Ethoxymethyl |
| Vinyl |
| Alllyl |
| Methallyl |
| Crotyl |
| Propargyl |
| Cinnamyl |
| 1-Methyl-2-propenyl |
| 1-Methyl-2-propynyl |
| Methoxy |
| Ethoxy |
| n-Propoxy |
| Isopropoxy |
| n-Butoxy |
| Isobutoxy |
| sec-Butoxy |
| tert-Butoxy |
| Methylthio |
| Ethylthio |
| Chlorodifluoromethoxy |
| Trifluoromethoxy |
| Chlorodifluoromethylthio |
| Trifluoromethylthio |
| Difluoromethoxy |
| Difluoromethylthio |
| Trichloromethoxy |
| Trichloromethylthio |
| Allyloxy |
| Allylthio |
| Propargyloxy |
| Propargylthio |
| Cyanomethyl |
| 2-Cyanoethyl |
| 1-Methyl-2-cyanoethyl |
| 1-Methyl-1-cyanoethyl |
| 1,1-Dimethyl-2-cyanoethyl |
| Methylsulfinyl |
| Ethylsulfinyl |
| n-Propylsulfinyl |
| Isopropylsulfinyl |
| Methylsulfonyl |
| Ethylsulfonyl |
| n-Propylsulfonyl |
| Isopropylsulfonyl |
| Trifluoromethylsulfonyl |

-continued

| R⁴ |
|---|
| Chloromethyl |
| 2-Chloroethyl |
| 1-Methyl-2-chloroethyl |
| 1-Methyl-1-chloroethyl |
| Nitro |
| Cyano |
| Phenyl |
| 2-F-phenyl |
| 3-F-phenyl |
| 4-F-phenyl |
| 2-Cl-phenyl |
| 3-Cl-phenyl |
| 4-Cl-phenyl |
| 2-CH₃-phenyl |
| 3-CH₃-phenyl |
| 4-CH₃-phenyl |
| 2-CF₃-phenyl |
| 3-CF₃-phenyl |
| 4-CF₃-phenyl |
| 2-OCH₃-phenyl |
| 3-OCH₃-phenyl |
| 4-OCH₃-phenyl |
| 2,4-Dichlorophenyl |
| Phenoxy |
| Phenylthio |
| 2-Cl-phenoxy |
| 3-Cl-phenoxy- |
| 4-Cl-phenoxy |
| 2,4-dichlorophenoxy |
| Benzyl |
| 2-Cl-benzyl |
| 3-Cl-benzyl |
| 4-Cl-benzyl |
| 2-Thienyl |
| 3-Thienyl |
| 2-Pyridyl |
| 3-Pyridyl |

For example, further compounds having the general structure

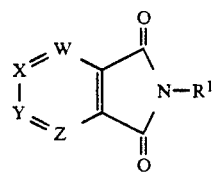

Ia

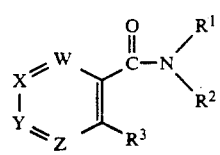

Ib

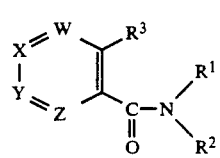

Ic where
W, X, Y or Z are together from one to 3 radicals C—R⁴, N or N→O, with the proviso that the ring contains a hetero atom and, for example,
R⁴ is a radical from the group consisting of $Q^1$ to $Q^{133}$,
R¹ is a radical from the group consisting of $L^1$ to $L^{200}$,
R² is a radical from the group consisting of $p^1$ to $p^{21}$,
R³ is formyl, 4,5-dihydrooxazol-2-yl or a radical —CO—AR⁵ or —CO—NR⁶R⁷;
A is oxygen or sulfur,
R⁵ is a radical from the group consisting of $M^1$ to $M^{90}$,
R⁶ and R⁷ independently of one another are each a radical from the group consisting of $S^1$ to $S^{15}$ or together form a radical from the group consisting of $S^{16}$ to $S^{19}$
and W, X, Y, Z, Q, L, P, M and S may be combined as desired,
can also be prepared in a similar manner.

R⁴, R¹, R², R⁵, R⁶ and R⁷ may be, for example, the following radicals:

| compound no. | R⁴ |
|---|---|
| Q1 | H |
| Q2 | F |
| Q3 | Cl |
| Q4 | Br |
| Q5 | I |
| Q6 | CH₃ |
| Q7 | C₂H₅ |
| Q8 | n-C₃H₇ |
| Q9 | i-C₃H₇ |
| Q10 | n-C₄H₉ |
| Q11 | i-C₄H₉ |
| Q12 | s-C₄H₉ |
| Q13 | tert.-C₄H₉ |
| Q14 | cyclo-C₃H₅ |
| Q15 | cyclo-C₄H₇ |
| Q16 | cyclo-C₅H₉ |
| Q17 | cyclo-C₆H₁₁ |
| Q18 | cyclo-C₇H₁₃ |
| Q19 | cyclo-C₈H₁₅ |
| Q20 | 1-Methyl-cyclo-C₃H₅ |
| Q21 | cyclo-C₃H₅-methyl |
| Q22 | 1-(cyclo-C₃H₅)-ethyl |
| Q23 | CHCl₂ |
| Q24 | CCl₃ |
| Q25 | CF₂Cl |
| Q26 | CF₃ |
| Q27 | C₂F₅ |
| Q28 | CF₂H |
| Q29 | CH₂OCH₃ |
| Q30 | CH(CH₃)OCH₃ |
| Q31 | CH(CH₃)OC₂H₅ |
| Q32 | CH(CH₃)CH₂—OCH₃ |
| Q33 | CH₂OC₂H₅ |
| Q34 | CH=CH₂ |
| Q35 | CH₂—CH=CH₂ |
| Q36 | CH(CH₃)CH=CH₂ |
| Q37 | CH₂CH=CH—CH₃ |
| Q38 | C≡CH |
| Q39 | C=CH—C₆H₅ |
| Q40 | C≡C—C₆H₅ |
| Q41 | CH(CH₃)C≡CH |
| Q42 | neo-C₅H₁₁ |
| Q43 | CH₃O |
| Q44 | C₂H₅O |
| Q45 | n-C₃H₇O |
| Q46 | i-C₃H₇O |
| Q47 | n-C₄H₉O |
| Q48 | s-C₄H₉O |
| Q49 | i-C₄H₉O |
| Q50 | tert.-C₄H₉O |
| Q51 | CH₃S |
| Q52 | C₂H₅S |
| Q53 | n-C₃H₇S |
| Q54 | i-C₃H₇S |
| Q55 | s-C₄H₉S |
| Q56 | tert.-C₄H₉S |
| Q57 | ClCF₂O |
| Q58 | CF₃O |
| Q59 | ClCF₂S |
| Q60 | CF₃S |
| Q61 | HCF₂O |
| Q62 | HCF₂S |
| Q63 | CCl₃O |
| Q64 | CCl₃S |
| Q65 | CH₂=CH—CH₂—O |
| Q66 | CH₂=CH—CH₂—S |
| Q67 | HC≡CH—CH₂—O |
| Q68 | HC≡CH—CH₂—S |
| Q69 | CH₂=CH—CH(CH₃)O |

| | -continued | | | -continued |
|---|---|---|---|---|
| Q70 | H—C≡CH—CH(CH₃)O | | L16 | n-C₇H₁₅ |
| Q71 | CH₂CN | | L17 | —CH(CH₃)C₅H₁₁ |
| Q72 | CH₂CH₂CN | | L18 | —CH(C₂H₅)C₄H₉ |
| Q73 | CH(CH₃)CH₂CN | | L19 | n-C₈H₁₇ |
| Q74 | C(CH₃)₂CN | | L20 | —CH(CH₃)C₆H₁₃ |
| Q75 | C(CH₃)₂CH₂CN | | L21 | —CH(C₂H₅)C₅H₁₁ |
| Q76 | CH₂Cl | | L22 | —C(CH₃)₂CH₂C(CH₃)₃ |
| Q77 | CH₂CH₂Cl | | L23 | cyclo-C₃H₅ |
| Q78 | CH(CH₃)CH₂Cl | | L24 | cyclo-C₄H₇ |
| Q79 | C(CH₃)₂Cl | | L25 | cyclo-C₅H₉ |
| Q80 | NO₂ | | L26 | cyclo-C₆H₁₁ |
| Q81 | CN | | L27 | cyclo-C₇H₁₃ |
| Q82 | C₆H₅ | | L28 | cyclo-C₈H₁₅ |
| Q83 | 2-F—C₆H₄ | | L29 | 1-Methylcyclohexyl |
| Q84 | 3-F—C₆H₄ | | L30 | 1-Ethylcyclohexyl |
| Q85 | 4-F—C₆H₄ | | L31 | 3,5-Dimethylcyclohexyl |
| Q86 | 2-Cl—C₆H₄ | | L32 | 3-Trifluoromethylcyclohexyl |
| Q87 | 3-Cl—C₆H₄ | | L33 | Tetrahydropyran-4-yl |
| Q88 | 4-Cl—C₆H₄ | | L34 | 4-Methyl-tetrahydropyran-2-yl |
| Q89 | 2-CH₃—C₆H₄ | | L35 | 4-Methyl-tetrahydropyran-4-yl |
| Q90 | 3-CH₃—C₆H₄ | | L36 | —CH₂—CH=CH₂ |
| Q91 | 4-CH₃—C₆H₄ | | L37 | —CH(CH₃)CH=CH₂ |
| Q92 | 2-CF₃—C₆H₄ | | L38 | —C(CH₃)₂CH=CH₂ |
| Q93 | 3-CF₃—C₆H₄ | | L39 | —C(CH₃, C₂H₅)CH=CH₂ |
| Q94 | 4-CF₃—C₆H₄ | | L40 | —C(CH₃)₂=C₂H₅ |
| Q95 | 2-OCH₃—C₆H₄ | | L41 | —C(CH₃, C₂H₅)C₂H₅ |
| Q96 | 3-OCH₃—C₆H₄ | | L42 | —C(CH₃)₂C₃H₇ |
| Q97 | 4-OCH₃—C₆H₄ | | L43 | —C(CH₃)₂cycloC₆H₁₁ |
| Q98 | 4-SCH₃—C₆H₄ | | L44 | —CH₂C(CH₃)=CH₂ |
| Q99 | 4-SCH₃—C₆H₄ | | L45 | —CH₂CH=CHCH₃ |
| Q100 | 4-NO₂—C₆H₄ | | L46 | —CH(CH₃)CH=CHCH₃ |
| Q101 | 4-CN₂—C₆H₄ | | L47 | —C(CH₃)₂CH=CHCH₃ |
| Q102 | 2,4-(Cl, Cl)—C₆H₄ | | L48 | —CH₂C≡CH |
| Q103 | 2,4-(CH₃, CH₃)—C₆H₄ | | L49 | —CH(CH₃)C≡CH |
| Q104 | C₆H₅O | | L50 | —C(CH₃)₂C≡CH |
| Q105 | C₆H₅S | | L51 | —C(CH₃, C₂H₅)C≡CH |
| Q106 | 2-Cl—C₆H₄O | | L52 | —C(C₂H₅)₂C≡CH |
| Q107 | 3-Cl—C₆H₄O | | L53 | —CH₂C≡CCH₃ |
| Q108 | 4-Cl—C₆H₄O | | L54 | —CH(CH₃)C≡CCH₃ |
| Q109 | C₆H₅—CH₂ | | L55 | —C(CH₃)₂C≡CCH₃ |
| Q110 | 2-Cl—C₆H₄—CH₂ | | L56 | —CH₂C₆H₅ |
| Q111 | 3-Cl—C₆H₄—CH₂ | | L57 | —CH(CH₃)C₆H₅ |
| Q112 | 4-Cl—C₆H₄—CH₂ | | L58 | —C(CH₃)₂C₆H₅ |
| Q113 | 4-F—C₆H₄—CH₂ | | L59 | —CH₂CH₂C₆H₅ |
| Q114 | 2-Thienyl | | L60 | —CH₂CH₂SCH₃ |
| Q115 | 3-Thienyl | | L61 | —CH(CH₃)CH₂SCH₃ |
| Q116 | 2-Furyl | | L62 | —C(CH₃)₂CH₂SCH₃ |
| Q117 | 3-Furyl | | L63 | —CH₂CH₂CH₂SCH₃ |
| Q118 | 1-Methyl-5-pyrazolyl | | L64 | —CH₂CH₂Cl |
| Q119 | 2-Oxazolyl | | L65 | —CH(CH₃)CH₂Cl |
| Q120 | 2-Thiazolyl | | L66 | —C(CH₃)₂CH₂Cl |
| Q121 | 2-Pyridyl | | L67 | —CH₂CH₂OCH₃ |
| Q122 | 3-Pyridyl | | L68 | —CH(CH₃)CH₂OCH₃ |
| Q123 | 4-Pyridyl | | L69 | —C(CH₃)₂CH₂OCH₃ |
| Q124 | 2-Tetrahydrofuryl | | L70 | —CH₂CH₂N(CH₃)₂ |
| Q125 | Methylsulfinyl | | L71 | —CH₂CH₂N(C₂H₅)₂ |
| Q126 | Ethylsulfinyl | | L72 | —CH₂CH₂CH₂OCH₃ |
| Q127 | n-Propylsulfinyl | | L73 | —CH₂CH₂CH₂N(CH₃)₂ |
| Q128 | i-Propylsulfinyl | | L74 | —CH₂CH₂CH₂N(C₂H₅)₂ |
| Q129 | Methylsulfonyl | | L75 | 2-CH₃—C₆H₄ |
| Q130 | Ethylsulfonyl | | L76 | 3-CH₃—C₆H₄ |
| Q131 | n-Propylsulfioyl | | L77 | 4-CH₃—C₆H₄ |
| Q132 | i-Propylsulfonyl | | L78 | 2-C₂H₅—C₆H₄ |
| Q133 | Trifluoromethylsulfinyl | | L79 | 3-C₂H₅—C₆H₄ |
| comp. no. | R¹ | | L80 | 4-C₂H₅—C₆H₄ |
| | | | L81 | 3-tert.-C₄H₉—C₆H₄ |
| L1 | H | | L82 | 4-tert.-C₄H₉—C₆H₄ |
| L2 | CH₃ | | L83 | 2,3-(CH₃)₂—C₆H₃ |
| L3 | C₂H₅ | | L84 | 2,4-(CH₃)₂—C₆H₃ |
| L4 | n-C₃H₇ | | L85 | 2,5-(CH₃)₂—C₆H₃ |
| L5 | i-C₃H₇ | | L86 | 2,6-(CH₃)₂—C₆H₃ |
| L6 | n-C₄H₉ | | L87 | 3,4-(CH₃)₂—C₆H₃ |
| L7 | i-C₄H₉ | | L88 | 3,5-(CH₃)₂—C₆H₃ |
| L8 | sec-C₄H₉ | | L89 | 2,3,4-(CH₃)₃—C₆H₂ |
| L9 | tert.-C₄H₉ | | L90 | 2,3,5-(CH₃)₃—C₆H₂ |
| L10 | n-C₅H₁₁ | | L91 | 2,4,5-(CH₃)₃—C₆H₂ |
| L11 | —CH(CH₃)C₃H₇ | | L92 | 2,4,6-(CH₃)₃—C₆H₂ |
| L12 | —CH(C₂H₅)C₂H₅ | | L93 | 3,4,5-(CH₃)₃—C₆H₂ |
| L13 | n-C₆H₁₃ | | L94 | 2-CF₃—C₆H₄ |
| L14 | —CH(CH₃)C₄H₉ | | L95 | 3-CF₃—C₆H₄ |
| L15 | —CH(C₂H₅)C₃H₇ | | L96 | 4-CF₃—C₆H₄ |
| | | | L97 | 2-F—C₆H₄ |

-continued

| | |
|---|---|
| L98 | 3-F—C₆H₄ |
| L99 | 4-F—C₆H₄ |
| L100 | 2-Cl—C₆H₄ |
| L101 | 3-Cl—C₆H₄ |
| L102 | 4-Cl—C₆H₄ |
| L103 | 2-Br—C₆H₄ |
| L104 | 3-Br—C₆H₄ |
| L105 | 4-Br—C₆H₄ |
| L106 | 2,3-F₂—C₆H₃ |
| L107 | 2,4-F₂—C₆H₃ |
| L108 | 2,5-F₂—C₆H₃ |
| L109 | 2,6-F₂—C₆H₃ |
| L110 | 2,3-Cl₂—C₆H₃ |
| L111 | 2,4-Cl₂—C₆H₃ |
| L112 | 2,5-Cl₂—C₆H₃ |
| L113 | 2,6-Cl₂—C₆H₃ |
| L114 | 3,4-Cl₂—C₆H₃ |
| L115 | 3,5-Cl₂—C₆H₃ |
| L116 | 2,3,4-Cl₃—C₆H₂ |
| L117 | 2,3,5-Cl₃—C₆H₂ |
| L118 | 2,4,6-Cl₃—C₆H₂ |
| L119 | 3,4,5-Cl₃—C₆H₂ |
| L120 | 2-CN—C₆H₄ |
| L121 | 3-CN—C₆H₄ |
| L122 | 4-CN—C₆H₄ |
| L123 | 2-OCH₃—C₆H₄ |
| L124 | 3-OCH₃—C₆H₄ |
| L125 | 4-OCH₃—C₆H₄ |
| L126 | 2-OC₂H₅—C₆H₄ |
| L127 | 3-OC₂H₅—C₆H₄ |
| L128 | 4-OC₂H₅—C₆H₄ |
| L129 | 2-O-n-C₃H₇—C₆H₄ |
| L130 | 3-O-n-C₃H₇—C₆H₄ |
| L131 | 4-O-n-C₃H₇—C₆H₄ |
| L132 | 2-O-i-C₃H₇—C₆H₄ |
| L133 | 3-O-i-C₃H₇—C₆H₄ |
| L134 | 4-O-i-C₃H₇—C₆H₄ |
| L135 | 2,3-(OCH₃)₂—C₆H₃ |
| L136 | 2,4-(OCH₃)₂—C₆H₃ |
| L137 | 2,5-(OCH₃)₂—C₆H₃ |
| L138 | 2,6-(OCH₃)₂—C₆H₃ |
| L139 | 3,4-(OCH₃)₂—C₆H₃ |
| L140 | 3,5-(OCH₃)₂—C₆H₃ |
| L141 | 3,4,5-(OCH₃)₃—C₆H₂ |
| L142 | 2-OCF₃—C₆H₄ |
| L143 | 3-OCF₃—C₆H₄ |
| L144 | 4-OCF₃—C₆H₄ |
| L145 | 2-OCF₂CHF₂—C₆H₄ |
| L146 | 3-OCF₂CHF₂—C₆H₄ |
| L147 | 4-OCF₂CHF₂—C₆H₄ |
| L148 | 2-SCH₃—C₆H₄ |
| L149 | 2-SCH₃—C₆H₄ |
| L150 | 4-SCH₃—C₆H₄ |
| L151 | 2-SC₂H₅—C₆H₄ |
| L152 | 3-SC₂H₅—C₆H₄ |
| L153 | 4-SC₂H₅—C₆H₄ |
| L154 | 2-S-i-C₃H₇—C₆H₄ |
| L155 | 3-S-i-C₃H₇—C₆H₄ |
| L156 | 4-S-i-C₃H₇—C₆H₄ |
| L157 | 2,4-(SCH₃)₂—C₆H₃ |
| L158 | 2-SCF₃—C₆H₄ |
| L159 | 3-SCF₃—C₆H₄ |
| L160 | 4-SCF₃—C₆H₄ |
| L161 | 2-NO₂—C₆H₄ |
| L162 | 3-NO₂—C₆H₄ |
| L163 | 4-NO₂—C₆H₄ |
| L164 | 2,3-(NO₂)₂—C₆H₃ |
| L165 | 2,4-(NO₂)₂—C₆H₃ |
| L166 | 2,5-(NO₂)₂—C₆H₃ |
| L167 | 2,6-(NO₂)₂—C₆H₃ |
| L168 | 3,4-(NO₂)₂—C₆H₃ |
| L169 | 3,5-(NO₂)₂—C₆H₃ |
| L170 | 2-CHO—C₆H₄ |
| L171 | 3-CHO—C₆H₄ |
| L172 | 4-CHO—C₆H₄ |
| L173 | 2-C(=O)CH₃—C₆H₄ |
| L174 | 3-C(=O)CH₃—C₆H₄ |
| L175 | 4-C(=O)CH₃—C₆H₄ |
| L176 | 2-C(=O)C₂H₅—C₆H₄ |
| L177 | 3-C(=O)C₂H₅—C₆H₄ |
| L178 | 4-C(=O)C₂H₅—C₆H₄ |
| L179 | 2-C(=O)-n-C₃H₇—C₆H₄ |
| L180 | 3-C(=O)-n-C₃H₇—C₆H₄ |
| L181 | 4-C(=O)-n-C₃H₇—C₆H₄ |
| L182 | 2-C(=O)CF₃—C₆H₄ |
| L183 | 3-C(=O)CF₃—C₆H₄ |
| L184 | 4-C(=O)CF₃—C₆H₄ |
| L185 | 1-Naphthyl |
| L186 | 2-Naphthyl |
| L187 | C₆H₅ |
| L188 | Piperidino |
| L189 | Tetrahydrofur-3-yl |
| L190 | Thiazol-2-yl |
| L191 | 5-Methyl-thiazol-2-yl |
| L192 | 5-Ethyl-thiazol-2-yl |
| L193 | 5-n-Propyl-thiazol-2-yl |
| L194 | 4-Methyl-5-carboxy-thiazol-2-yl |
| L195 | Cyclopropylmethyl |
| L196 | 1-(Cyclopropyl)-ethyl |
| L197 | CH(CH₃)CH₂CN |
| L198 | C(CH₃)₂CN |
| L199 | C(CH₃)₂CH₂CN |
| L200 | C(CH₃)₂CH₂F |

| comp. no. | R² |
|---|---|
| P1 | H |
| P2 | CH₃ |
| P3 | C₂H₅ |
| P4 | n-C₃H₇ |
| P5 | i-C₃H₇ |
| P6 | n-C₄H₉ |
| P7 | s-C₄H₉ |
| P8 | t-C₄H₉ |
| P9 | CH₂—CH₂OH |
| P10 | CH₂—CH₂Cl |
| P11 | CH₂OCH₃ |
| P12 | CH₂OC₂H₅ |
| P13 | CH₂CH₂OCH₃ |
| P14 | CH₂SCH₃ |
| P15 | CH₂SC₂H₅ |
| P16 | CH₂CH₂SCH₃ |
| P17 | CH₂—CH₂—N(CH₃)₂ |
| P18 | CH₂CH₂—N(C₂H₅)₂ |
| P19 | cyclo-C₃H₅ |
| P20 | cyclo-C₆H₁₁ |

| comp. no. | R⁵ |
|---|---|
| P21 | 1-Methyl-cyclo-C₆H₁₀ |
| M1 | H |
| M2 | CH₃ |
| M3 | C₂H₅ |
| M4 | n-C₃H₇ |
| M5 | i-C₃H₇ |
| M6 | n-C₄H₉ |
| M7 | s-C₄H₉ |
| M8 | t-C₄H₉ |
| M9 | CH(CH₃)C₆H₁₃ |
| M10 | CH₂CH₂OCH₃ |
| M11 | CH₂CH₂OC₂H₅ |
| M12 | Succinimido |
| M13 | Li⊕ |
| M14 | Na⊕ |
| M15 | K⊕ |
| M16 | NH₄⊕ |
| M17 | H₃N⊕i-C₃H₇ |
| M18 | H₂N⊕(i-C₃H₇)₂ |
| M19 | H₃N⊕CH₂CH₂OH |
| M20 | CH₂CH=CH₂ |
| M21 | CH₂—C(CH₃)=CH₂ |
| M22 | CH₂—C(Cl)=CH₂ |
| M23 | CH₂—C≡CH |
| M24 | CH₂—C≡C—CH₂OH |
| M25 | —N=C(CH₃)₂ |
| M26 | —N=C(C₂H₅)₂ |
| M27 | CH₂—CH₂—N(CH₃)₂ |
| M28 | CH₂—CH₂—N(C₂H₅)₂ |
| M29 | CH₂—CH₂N⊕(CH₃)₃I⊖ |
| M30 | CH₂—CF₃ |
| M31 | Phenyl |
| M32 | Phenylethyl |
| M33 | CH₂—CH₂Si(CH₃)₃ |
| M34 | CH₂—CH₂ON=C(CH₃)₂ |
| M35 | CH₂—PO(OC₂H₅)₂ |
| M36 | CH(CH₃)CH₂OCH₃ |
| M37 | CH₂—CON(C₂H₅)₂ |
| M38 | CH₂CH₂—N(C₂H₅)₂ |
| M39 | CH₂—OCH₂C₆H₅ |
| M40 | CH₂COOCH₃ |
| M41 | —N=C(cyclo-C₃H₅)₂ |
| M42 | —N=C(CH₃)(C₂H₅) |
| M43 | Cyclohexanimino |
| M44 | Cyclooctanimino |
| M45 | CH₂—CH₂—Cl |
| M46 | CH₂—CH₂—CN |
| M47 | CH₂—CCl₃ |
| M48 | Pyrid-3-ylmethyl |
| M49 | Thien-2-yl-methyl |
| M50 | CH₂CH₂OCH₂CH₂OCH₃ |
| M51 | —CH₂—CH(OH)—CH₂—OH |
| M52 | CH₂CH₂OCH₂CH₂O—CH₂CH₃ |
| M53 | —CH(C₆H₅)CO₂CH₃ |
| M54 | cyclo-C₆H₁₁ |
| M55 | —CH₂—OCH₂—(4-Cl—C₆H₄) |
| M56 | Tetrahydropyran-2-yl |
| M57 | Tetrahydrofur-2-yl |
| M58 | (4-Bromo-benzoyl)methyl |
| M59 | (4-Methoxybenzoyl)methyl |
| M60 | CH₂—CH₂COOCH₃ |
| M61 | Phthalimidomethyl |
| M62 | Fur-2-ylmethyl |
| M63 | Tetrahydrofur-2-yl-methyl |
| M64 | Pyrid-2-yl-methyl |
| M65 | Pyrid-4-yl-methyl |
| M66 | Pyrid-3-yl-methyl |
| M67 | Thien-2-yl-methyl |
| M68 | —CH(C₆H₅)COOCH₃ |
| M69 | Piperidino |
| M70 | Phthalimido |
| M71 | Benzotriazol-1-yl |
| M72 | —N=CH—C₆H₅ |
| M73 | Fur-2-yl-methylenimino |
| M74 | 2-NO₂-4-F—C₆H₃ |
| M75 | 3,5-(CF₃)₂—C₆H₃ |
| M76 | CH₂—CH₂—S—CH₃ |
| M77 | 4-NHCOCH₃—C₆H₄ |
| M78 | 2,4-Dichlorobenzyl |
| M79 | cyclo-C₃H₅ |
| M80 | 1-(cyclo-C₃H₇)-ethyl |
| M81 | CH(CH₃)CH=CH₂ |
| M82 | CH(CH₃)CH₂CN |
| M83 | C(CH₃)₂CN |
| M84 | CH(CH₃)CH₂Cl |
| M85 | C(CH₃)₂CH₂Cl |
| M86 | CH₂CH₂O—CH₂CO₂CH₃ |
| M87 | CH₂CH₂—OCH(CH₃)CO₂CH₃ |
| M88 | CH₂CH₂OCH(CH₃)CO₂C₂H₅ |
| M89 | CH(CH₃)CO₂CH₂CO₂CH₃ |
| M90 | CH(CH₃)CO₂CH(CH₃)CO₂CH₃ |

| comp. no. | R⁶ and R⁷ independently of one another |
|---|---|
| S1 | H |
| S2 | CH₃ |
| S3 | C₂H₅ |
| S4 | n-C₃H₇ |
| S5 | i-C₃H₇ |
| S6 | cyclo-C₃H₅ |
| S7 | n-C₄H₉ |
| S8 | i-C₄H₉ |
| S9 | s-C₄H₉ |
| S10 | tert.-C₄H₉ |
| S11 | cyclo-C₅H₉ |
| S12 | cyclo-C₆H₁₁ |
| S13 | C₅H₅ |
| S14 | 2-Furyl |
| S15 | 3-Furyl |
| S16 | (CH₂)₄* |
| S17 | (CH₂)₅* |
| S18 | (CH₂)₆* |
| S19 | (CH₂)₇* |

*(R⁶ and R⁷ together)

PREPARATION EXAMPLES 1. 2-Isopropylaminocarbonyl-5-methylpyridine-3-carboxylic acid 3.25 g of isopropylamine are added to 8.1 g of 5-methylpyridine-2,3-dicarboxylic anhydride in 50 ml of methylene chloride at from 20° to 30° C. while stirring, and the stirred mixture is refluxed for 3 hours. The reaction mixture is evaporated down under reduced pressure and the residue is stirred in a 1:1:1 mixture of ether, methyl tert-butyl ether and petroleum ether. Filtration under suction and drying give 10.1 g of the title compound as colorless crystals of melting point 95°–105° C.

ACTIVE INGREDIENT EXAMPLE NO. 1.026

2. N-isopropyl-5-methylpyridine-2,3-dicarboximide 3 g of the carboxylic acid from 1. in 30 ml of acetic anhydride are refluxed for 3 hours while stirring. The reaction mixture is evaporated down under reduced pressure, the residue is stirred with water and taken up in methylene chloride and the solution is dried over magnesium sulfate. Chromatography over alumina, evaporation under reduced pressure and washing with 1:1 petroleum ether/ether give 2.3 g of the title compound of melting point 127°–128° C.

ACTIVE INGREDIENT EXAMPLE NO. 3.05

3. a) 2-Carbomethoxy-6-methylpyridine-3-carboxylic acid 48.9 g of 6-methylpyridine-2,3-dicarboxylic anhydride in 200 ml of methanol are refluxed for 3 hours while stirring. Evaporating down the mixture under reduced pressure gives 57.9 g of the title compound of melting point 133°-158° C. (decomposition).

b) 2-Carbomethoxy-6-methylpyridine-3-carbonyl chloride 44 g of thionyl chloride are added to 57.7 g of the carboxylic acid from a) in 250 ml of 1,2-dichloroethane at 60° C. while stirring, and the mixture is refluxed for 6 hours. 64 g of the title compound are obtained as a semicrystalline mass. According to the NMR spectrum, it contains about 20% of the isomeric 3-carbomethoxy compound.

c) N-sec-butyl-6-methylpyridine-2,3-dicarboximide 43 g of sec-butylamine are added dropwise to 64 g of the acyl chloride from b) in 300 ml of methylene chloride at from 15° to 20° C. while stirring, and stirring is continued for 12 hours at 25° C. Washing with water and evaporating down under reduced pressure give 43 g of a semicrystalline mass. The latter is dissolved in methylene chloride and the solution is stirred over active carbon and then chromatographed over alumina. 36 g of the title compound are obtained as colorless crystals of melting point 105°-106° C.

ACTIVE INGREDIENT EXAMPLE NO. 3.017

4. 2-(2-Chlorophenyl)-aminocarbonyl-6-methylpyridine-3-carboxylic acid 54.5 g of the title compound of melting point 155°-160° C. are obtained from 32.6 g of 6-methylpyridine-2,3-dicarboxylic anhydride and 28.1 g of 2-chloroaniline by the method used in 1.

ACTIVE INGREDIENT EXAMPLE NO. 1.010

5. Methyl 2-(2-chlorophenyl)-aminocarbonyl-6-methylpyridine-3-carboxylate 12.8 g of N,N-dicyclohexylcarbodiimide are added to a mixture of 15 g of carboxylic acid from 4., 100 ml of diisopropyl ether and 50 ml of methanol at from 15° to 20° C., and stirring is carried out for 3 hours at 50° C. The precipitated urea is filtered off under suction, the filtrate is evaporated down under reduced pressure and the residue is chromatographed over alumina. Washing with pentane gives 7.5 g of the title compound as colorless crystals of melting point 105°-107° C.

ACTIVE INGREDIENT EXAMPLE NO. 1.007

6. N-sec-butyl-5-methylpyridine-2,3-dicarboximide is obtained as colorless crystals of melting point 96°-99° C. in the preparation by the methods of Preparation Examples 1 and 2 in ring cleavage of pyridine-2,3-dicarboxylic anhydride with sec-butylamine and subsequent cyclization in acetic anhydride.

ACTIVE INGREDIENT EXAMPLE NO. 3.018

7. Methyl 2-sec-butylaminocarbonyl-5-methylpyridine-3-carboxylate 3 g of triethylamine are added dropwise to 4.3 g of the imide from 6. in 130 ml of methanol at from 20° to 25° C., and the mixture is stirred for 2 hours at 50° C. The reaction mixture is evaporated down under reduced pressure, the residue is taken up in methylene chloride and the solution is chromatographed over silica gel. 2.8 g of the title compound of melting point 58°-60° C. are obtained as colorless crystals.

ACTIVE INGREDIENT EXAMPLE NO. 1.023

8. 2-Sec-butylaminocarbonyl-5-methylpyridine-3-carboxamide 8 g of gaseous ammonia are passed into a solution of 10 g of the imide from 6. in 200 ml of isopropanol in the course of one hour at 0° C., and stirring is carried out for 12 hours at 25° C. The mixture is evaporated down under reduced pressure and the residue is stirred with methyl tert-butyl ether. 8.3 g of the title compound of melting point 119°-123° C. are obtained. According to the NMR spectrum, 20% of the isomeric 3-sec-butylaminocarbonyl compound was formed at the same time.

ACTIVE INGREDIENT EXAMPLE NO. 7.003

9. 2-Tert-butylaminocarbonyl-6-methylpyridine-3-carboxylic acid is obtained as colorless crystals of melting point 100°-102° C. on ring cleavage of 6-methylpyridine-2,3-dicarboxylic anhydride with tert-butylamine by the method of Preparation Example 1.

ACTIVE INGREDIENT EXAMPLE NO. 1.003

10. Tri-n-butylammonium 2-tert-butylaminocarbonyl-6-methylpyridine-3-carboxylate 8.5 g of tri-n-butylamine are added to 9.4 g of the carboxylic acid from 9. in 100 ml of methylene chloride at from 20° to 24° C. in the course of 10 minutes while stirring, and stirring is continued for a further 10 minutes. The reaction mixture is partitioned between water and saturated sodium chloride solution. The organic phase is dried and evaporated down under reduced pressure and the residue is stirred with ether to give 17.7 g of the title compound of melting point 85°-87° C.

ACTIVE INGREDIENT EXAMPLE NO. 1.020

11. N-isopropylpyridine-2,3-dicarboximide-1-oxide 79.7 g of 55% strength 3-chloroperbenzoic acid are added to 22 g of N-isopropylpyridine-2,3-dicarboximide in 100 ml of methylene chloride in the course of 2 hours while refluxing and stirring, and stirring is continued for a further 2 hours. The reaction mixture is extracted three times with 10% strength sodium carbonate solution and then with water and saturated sodium chloride solution, dried, and evaporated down under reduced pressure. The residue is stirred with methyl tert-butyl ether, 11.2 g of the title compound of melting point 138°-142° C. being obtained.

ACTIVE INGREDIENT EXAMPLE NO. 5.003

12. N-isopropyl-6-chloropyridine-2,3-dicarboximide 6.5 g of the imide from 11. are added a little at a time to 100 ml of phosphorus oxychloride, and the mixture is heated stepwise until it refluxes and is stirred for 5 hours. The reaction mixture is evaporated down under reduced pressure, the residue is stirred with water and is taken up in methylene chloride, and the solution is washed in succession with 10% strength sodium carbonate solution, with water and with saturated sodium chloride solution. Evaporation gives 4.1 g of the title compound as colorless crystals of melting point 122°-123° C.

ACTIVE INGREDIENT EXAMPLE NO. 3.023

13. N-isopropylpyridine-3,4-dicarboximide-1-oxide

The title compound is obtained as colorless crystals of melting point 169°-173° C. by the method of Preparation Example 11, in the oxidation of the N-isopropyl-3,4-dicarboximide with 3-chloroperbenzoic acid.

ACTIVE INGREDIENT EXAMPLE NO. 6.001

14. N-isopropyl-6-chloropyridine-3,4-dicarboximide

The title compound is obtained as colorless crystals of melting point 94°-96° C. by the method of Preparation Example 12 on reacting the N-oxide from 13. with phosphorus oxychloride. According to the NMR spectrum, about 15% of the isomeric 1-chloro compound was formed at the same time.

ACTIVE INGREDIENT EXAMPLE NO. 4.006

15. N-isopropyl-6-methoxypyridine-3,4-dicarboximide 12 g of 30% strength sodium methylate solution are added to 5 g of the chlorine compound from 14. in 100 ml of methanol, and the mixture is refluxed for 16 hours. The reaction mixture is evaporated down under reduced pressure and then partitioned between water/methylene chloride. The organic phase is evaporated down and the residue is stirred with ether/petroleum ether to give 1.6 g of the title compound of melting point 150°-152° C.

ACTIVE INGREDIENT EXAMPLE NO. 4.011

The aqueous phase is neutralized with concentrated hydrochloric acid and evaporated down and the residue is stirred with methanol. The organic extract is evaporated down to give 4.4 g of sodium 3-isopropylaminocarbonyl-6-methoxypyridine-4-carboxylate of melting point 56° C. (decomposition).

ACTIVE INGREDIENT EXAMPLE NO. 2.007

16. a) 6-Trichloromethylpyridine-2,3-dicarboxylic anhydride

A mixture of 200 g of 6-methylpyridine-2,3-dicarboxylic anhydride and 600 ml of 1,2-dichlorobenzene is gassed at 120° C. for about 1 hour with hydrogen chloride, after which 2 g of α,α-azoisobutyronitrile are added and chlorine gas is passed in over 10 hours. The reaction solution is evaporated down and the residue is stirred with n-pentane. 311.6 g of the title compound are obtained as colorless crystals of melting point 126°-127° C.

b) 6-Chlorodifluoromethylpyridine-2,3-dicarboxylic anhydride

A stirred mixture of 53.3 g of the anhydride of a) and 39.3 g of antimony(III) fluoride is heated to 120° C. and 5 ml of antimony(V) chloride are then slowly added, the exothermic reaction being slowed down at 130° C. by removing the heating bath. Stirring is continued for a further 30 minutes at 125° C., the mixture is cooled and 100 ml of 1,2-dichloroethane are added. 100 ml of 6N hydrochloric acid are then slowly run in at from 0° to 10° C. and the aqueous phase is extracted with twice 100 ml of methylene chloride. The organic extract is washed once with 6 N hydrochloric acid. Drying and evaporation give 29.5 g of the title compound as a yellowish oil [IR: C=O 1796 cm⁻¹].

c) 2-Tert-butylaminocarbonyl-6-chlorodifluoromethylpyridine-3-carboxylic acid 28.5 g of the title compound are obtained as a colorless mass from 23.4 g of the anhydride from b) and 8 g of tert-butylamine in 200 ml of dioxane by the method of Preparation Example 1; $^1$H-NMR (CDCl$_3$) [ppm] 1.52 (s, 9H), 7.9 (d, 1H), 8.8 (d, 1H).

ACTIVE INGREDIENT EXAMPLE NO. 1.027

17. N-tert-butyl-6-chlorodifluoromethylpyridine-2,3-dicarboximide 15.5 g of the title compound are obtained as colorless crystals of melting point 138°-140° C. from 28.3 g of the amide from 16 c) in 300 ml of acetic anhydride by the method of Preparation Example 2.

ACTIVE INGREDIENT EXAMPLE NO. 3.031

18. N-tert-butyl-6-chloromethylpyridine-3,4-dicarboximide 31.5 g of N-tert-butyl-6-methylpyridine-3,4-dicarboximide-1-oxide from 6.004 are added a little at a time to 300 ml of phosphorus oxychloride, and the mixture is heated stepwise until it refluxes and is stirred for 3 hours. The reaction mixture is evaporated down under reduced pressure, the residue is taken up in methylene chloride and the solution is stirred into ice water. The organic phase is washed several times with water, dried, filtered over alumina and evaporated down under reduced pressure. 28.9 g of the title compound of melting point 62°-64° C. are obtained.

ACTIVE INGREDIENT EXAMPLE NO. 4.010

19. Methyl 4-tert-butylaminocarbonyl-6-methoxymethylpyridine-3-carboxylate 44.8 g of 30% strength sodium methylate solution are added to 21.0 g of the imide from 18. in 250 ml of methanol at from 25° to 30° C. in the course of 15 minutes while stirring, and the mixture is refluxed for 6 hours. After cooling, the mixture is brought to a pH of about 6.5 with 2N methanolic hydrochloric acid and the precipitated sodium chloride is filtered off under suction. The filtrate is evaporated down under reduced pressure and the residue is triturated with 3:1 methyl tert-butyl ether/petroleum ether to give 15.6 g of the title compound of melting point 138°-142° C.

ACTIVE INGREDIENT EXAMPLE NO. 9.001

The pyridine derivatives of the formulae Ia, Ib and Ic listed in the Tables below were obtained by these processes described in Examples 1 to 19.

TABLE 1

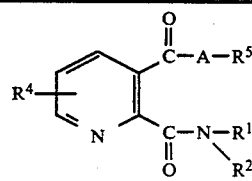

Ic

| No. | R$^1$ | R$^2$ | R$^4$ | R$^5$ | A | phys. data mp.(°C.), IR(cm⁻¹), NMR(ppm) |
|---|---|---|---|---|---|---|
| 1.001 | i-C$_3$H$_7$ | H | H | H | O | 130-136 decomp. |

TABLE 1-continued

Structure Ic: pyridine with R⁴ substituent, C(=O)-A-R⁵ group and C(=O)-N(R¹)(R²) group

| No. | R¹ | R² | R⁴ | R⁵ | A | phys. data mp.(°C.), IR(cm⁻¹), NMR(ppm) |
|---|---|---|---|---|---|---|
| 1.002 | i-C₃H₇ | H | 6-CH₃ | H | O | 74–75 |
| 1.003 | tert.-C₄H₉ | H | 6-CH₃ | H | O | 100–102 decomp. |
| 1.004 | 3-Cl-Phenyl | H | 6-CH₃ | H | O | 162 decomp. |
| 1.005 | tert.-C₄H₉ | H | 5-C₂H₅ | H | O | 60 |
| 1.006 | 3-Cl-Phenyl | H | H | H | O | 155 decomp. |
| 1.007 | 2-Cl-Phenyl | H | 6-CH₃ | CH₃ | O | 105–107 |
| 1.008 | C₂H₅ | H | H | H | O | 116 decomp. |
| 1.009 | i-C₃H₇ | H | 5-C₂H₅ | H | O | 113–118 |
| 1.010 | 2-Cl-Phenyl | H | 6-CH₃ | H | O | 155–160 |
| 1.011 | tert.-C₄H₉ | H | H | CH₃ | O | 70–71 |
| 1.012 | cyclo-Propyl | H | 6-CH₃ | H | O | 75–80 |
| 1.013 | sec.-C₄H₉ | H | 6-CH₃ | H | O | resin IR: C=O 1718, 1662 |
| 1.014 | tert.-C₄H₉ | H | 6-CH₃ | CH₃ | O | 84–87 |
| 1.015 | 4-Cl-Phenyl | H | 6-CH₃ | H | O | 140–147 |
| 1.016 | Phenyl | H | 6-CH₃ | H | O | 135–142 |
| 1.017 | tert.-C₄H₉ | H | 6-CCl₃ | H | O | 107–109 |
| 1.018 | 4-Cl-Phenyl | H | 6-CCl₃ | H | O | 200 decomp. |
| 1.019 | tert.-C₄H₉ | H | 5-CH₃ | H | O | 105 decomp. |
| 1.020 | tert.-C₄H₉ | H | 6-CH₃ | HN⊕[n-C₄H₉]₃ | O | 85–87 |
| 1.021 | tert.-C₄H₉ | H | 5-CCl₃ | H | O | 121–125 |
| 1.022 | sec.-C₄H₉ | H | 6-CH₃ | CH₃ | O | oel IR: C=O 1736, 1674 |
| 1.023 | sec.-C₄H₉ | H | 5-CH₃ | CH₃ | O | 58–60 |
| 1.024 | i-C₄H₉ | H | 5-CH₃ | CH₃ | O | oel IR: C=O 1736, 1674 |
| 1.025 | i-C₄H₉ | H | 5-CH₃ | H | O | 65–70 |
| 1.026 | i-C₃H₇ | H | 5-CH₃ | H | O | 95–105 |
| 1.027 | tert.-C₄H₉ | H | 6-CF₂Cl | H | O | resin ¹H-NMR(CDCl₃) 1, 52(s; 9H), 7, 9(d; 1H) 8, 8(d; 1H) |
| 1.028 | i-C₃H₇ | H | H-CH₃ | CH₃ | O | resin; IR: C=O 1736, 1716, 1706, 1677 |
| 1.029 | 1-cyclo-Propyl-ethyl | H | 6-CH₃ | CH₃ | O | $n_D^{23} = 1.5300$ |
| 1.030 | tert.-C₄H₉ | H | 6-O—CH₃ | CH₃ | O | 82–84 |
| 1.031 | sec.-C₄H₉ | H | 6-tert.-C₄H₉ | CH₃ | O | $n_D^{24} = 1.5300$ |
| 1.032 | sec.-C₄H₉ | H | 6-tert.-C₄H₉ | CH₃ | O | 78–83 |
| 1.033 | sec.-C₄H₉ | H | 5-i-C₃—H₇ | H | O | 28–32 |
| 1.034 | tert.-C₄H₉ | H | 5-i-C₃—H₇ | H | O | 127–131 |
| 1.035 | sec.-C₄H₉ | H | 5-C₃—H₇, 6-O—CH₃ | CH₃ | O | 105 |
| 1.036 | tert.-C₄H₉ | H | 5-C₂—H₅, 6-OCH₃ | CH₃ | O | 136 decomp. |
| 1.037 | tert.-C₄H₉ | H | 5-C₂—H₅, 6-Cl | H | O | 172–175 |

TABLE 2

Structure Ic (isomer)

| No. | R¹ | R² | R⁴ | R⁵ | A | mp.(°C.) |
|---|---|---|---|---|---|---|
| 2.001 | tert.-C₄H₉ | H | H | H | O | 144–148 as a mixture with 25% of isomeric 4-amide |
| 2.002 | i-C₃H₇ | H | H | H | O | 155–161 as a mixture with 33% of isomeric 4-amide |
| 2.003 | sec.-C₄H₉ | H | H | H | O | 186–189 as a mixture with 33% of isomeric 4-amide |
| 2.004 | tert.-C₄H₉ | H | 6-CH₃ | H | O | 191 (decomp.) as a mixture with 34% of isomeric 4-amide |

TABLE 2-continued

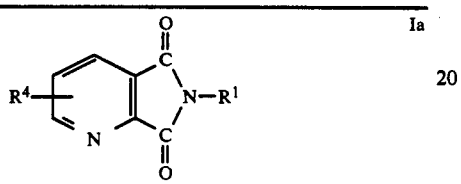

Ic

| No. | R¹ | R² | R⁴ | R⁵ | A | mp.(°C.) |
|---|---|---|---|---|---|---|
| 2.005 | i-C₃H₇ | H | 6-CH₃ | H | O | 183 (decomp.) as a mixture with 30% of isomeric 4-amide |
| 2.006 | tert.-C₄H₉ | H | 6-OCH₃ | CH₃ | O | 108–111 |
| 2.007 | i-C₃H₇ | H | 6-OCH₃ | Na | O | 56 (decomp.) |

TABLE 3

Ia

| No. | R¹ | R⁴ | phys. data mp.(°C.), IR(cm⁻¹) |
|---|---|---|---|
| 3.001 | tert.-C₄H₉ | H | 58–60 |
| 3.002 | i-C₃H₇ | H | 102–104 |
| 3.003 | tert.-C₄H₉ | 6-CH₃ | 160–161 |
| 3.004 | i-C₃H₇ | 6-CH₃ | 153–154 |
| 3.005 | i-C₃H₇ | 5-CH₃ | 127–128 |
| 3.006 | tert.-C₄H₉ | 5-CH₃ | 120–121 |
| 3.007 | 3-Cl-Phenyl | H | 188–190 |
| 3.008 | Phenyl | 6-CH₃ | 200–205 |
| 3.009 | C₂H₅ | 6-CH₃ | 169–170 |
| 3.010 | tert.-C₄H₉ | 5-C₂H₅ | 82–83 |
| 3.011 | 3-Cl-Phenyl | 6-CH₃ | 211–212 |
| 3.012 | C₂H₅ | H | 109–111 |
| 3.013 | 4-Cl-Phenyl | 6-CH₃ | 244–245 |
| 3.014 | i-C₃H₇ | 6-C₂H₅ | 104–105 |
| 3.015 | cyclo-Propyl | 6-CH₃ | 174–175 |
| 3.016 | 2-Cl-Phenyl | 6-CH₃ | 250–253 |
| 3.017 | sec.-C₄H₉ | 6-CH₃ | 105–106 |
| 3.018 | sec.-C₄H₉ | 5-CH₃ | 96–99 |
| 3.019 | 4-Cl-Phenyl | 6-CCl₃ | 181–182 |
| 3.020 | sec.-C₄H₉ | H | 52–53 |
| 3.021 | tert.-C₄H₉ | 6-CCl₃ | 148–149 |
| 3.022 | tert.-C₄H₉ | 6-Cl | 127–129 |
| 3.023 | i-C₃H₇ | 6-Cl | 122–123 |
| 3.024 | sec.-C₄H₉ | 6-Cl | 78–80 |
| 3.025 | sec.-C₄H₉ | 5-CH₃, 6-Cl | 104–105 |
| 3.026 | tert.-C₄H₉ | 5-C₂H₅, 6-Cl | 135–136 |
| 3.027 | tert.-C₄H₉ | 5-CH₃, 6-Cl | 118–121 |
| 3.028 | tert.-C₄H₉ | 5-CCl₃ | 76–81 |
| 3.029 | tert.-C₄H₉ | 5-CH₃, 6-CH₃ | 146–149 |
| 3.030 | sec.-C₄H₉ | 5-CCl₃ | resin IR: C=O 1720 |
| 3.031 | tert.-C₄H₉ | 6-CF₂Cl | 139–140 |
| 3.032 | i-C₄H₉ | 5-CH₃ | 148–151 |
| 3.033 | i-C₄H₉ | H | 93–97 |
| 3.034 | tert.-C₄H₉ | 4-CH₃ | 131–132 |
| 3.035 | i-C₃H₇ | 4-CH₃ | 89–90 |
| 3.036 | 1-(cyclo-Propyl)ethyl | 6-CH₃ | 110–112 |
| 3.037 | tert.-C₄H₉ | 4-C₂H₅ | 130–132 |
| 3.038 | i-C₃H₇ | 4-C₂H₅ | 84–87 |
| 3.039 | i-C₃H₇ | H-CH₃, 6-Cl | 101–103 |
| 3.040 | sec.-tert.-C₄H₉ | 6-tert.-C₄H₉ | n_D²³ = 1.5211 |
| 3.041 | tert.-C₄H₉ | 6-tert.-C₄H₉ | 63–67 |
| 3.042 | tert.-C₄H₉ | 6-OCH₃ | 131–133 |
| 3.043 | tert.-C₄H₉ | 6-CF₃ | 82–87 |
| 3.044 | tert.-C₄H₉ | 5-tert.-C₄H₉ | 128–132 |
| 3.045 | sec.-C₄H₉ | 5-i-C₃H₇ | n_D²³ = 1.5300 |
| 3.046 | tert.-C₄H₉ | 5-i-C₃H₇ | 60–62 |
| 3.047 | i-C₃H₇ | 5-CH₂—C₆H₅ | 64–67 |
| 3.048 | tert.-C₄H₉ | 5-CH₂—C₆H₅ | n_D²³ = 1.5779 |
| 3.049 | tert.-C₄H₉ | 5-i-C₃H₇, | 93–95 |

TABLE 3-continued

Ia

| No. | R¹ | R⁴ | phys. data mp.(°C.), IR(cm⁻¹) |
|---|---|---|---|
| 3.050 | sec.-C₄H₉ | 6-Cl 6-OCH₃ | 91–95 |
| 3.051 | C(CH₃)₂—C₂H₅ | 5-CH₃, 6-CH₃ | 84–87 |
| 3.052 | sec.-C₄H₉ | 5-i-C₃H₇ 6-OCH₃ | n_D²³ = 1.5361 |
| 3.053 | tert.-C₄H₉ | 5-C₂H₅, 6-SO₂CH₃ | 105–107 |
| 3.054 | tert.-C₄H₉ | 5-C₂H₅, 6-SCH₃ | 93–97 |
| 3.055 | tert.-C₄H₉ | 5-C₂H₅, 6-OCH₃ | 94–97 |
| 3.056 | C(CH₃)₂-i-C₃H₇ | 5-CH₃, 6-OCH₃ | 125–130 |
| 3.057 | sec.-C₄H₉ | 5-CH₃, 6-OCH₃ | 104–106 |
| 3.058 | tert.-C₄H₉ | 5-CH₃, 6-OCH₃ | 124–127 |
| 3.059 | tert.-C₄H₉ | 6-OCH₂CH=CH₂ | 52–57 |
| 3.060 | C(CH₃)(i-C₃H₇)CN | H | 92–96 |
| 3.061 | C(CH₃)(CH₂OCH₃)CN | H | 152–156 |

TABLE 4

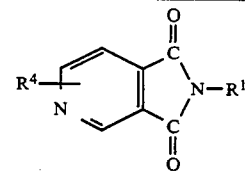

Ia

| No. | R¹ | R⁴ | phys. data mp.(°C.), IR(cm⁻¹) |
|---|---|---|---|
| 4.001 | i-C₃H₇ | H | 103–106 |
| 4.002 | sec.-C₄H₉ | H | oel IR: C=O 1716 |
| 4.003 | tert.-C₄H₉ | H | 46–49 |
| 4.004 | tert.-C₄H₉ | 6-Cl | 73–76 |
| 4.005 | sec.-C₄H₉ | 6-Cl | 30–35 |
| 4.006 | i-C₃H₇ | 6-Cl | 94–96 |
| 4.007 | tert.-C₄H₉ | 6-CH₃ | 89–91 |
| 4.008 | i-C₃H₇ | 6-CH₃ | 91–94 |
| 4.009 | i-C₃H₇ | 6-CH₂Cl | 63–65 |
| 4.010 | tert.-C₄H₉ | 6-CH₂Cl | 62–64 |
| 4.011 | i-C₃H₇ | 6-OCH₃ | 150–152 |
| 4.012 | tert.-C₄H₉ | 6-O—CH₃ | 101–103 |
| 4.013 | tert.-C₄H₉ | 6-CH₂—O—CH₃ | 38–41 |
| 4.014 | n-C₃H₇ | 2,6-Cl₂ | 74–78 |
| 4.015 | C(CH₃)₂CN | H | 84–86 |

TABLE 5

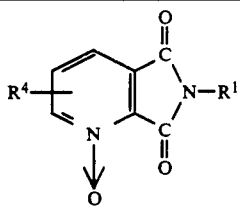

| No. | R¹ | R⁴ | mp.(°C.) |
|---|---|---|---|
| 5.001 | sec.-C₄H₉ | H | 103–104 |
| 5.002 | tert.-C₄H₉ | H | 118–122 |
| 5.003 | i-C₃H₇ | H | 138–142 |
| 5.004 | tert.-C₄H₉ | 5-CH₃ | 118–122 |
| 5.005 | tert.-C₄H₉ | 5-C₂H₅ | 128–131 |
| 5.006 | sec.-C₄H₉ | 5-CH₃ | 195–198 |

TABLE 6

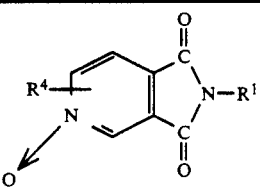

| No. | R¹ | R⁴ | mp.(°C.) |
|---|---|---|---|
| 6.001 | i-C₃H₇ | H | 172–174 |
| 6.002 | tert.-C₄H₉ | H | 194–199 |
| 6.003 | sec.-C₄H₉ | H | 120–125 |
| 6.004 | tert.-C₄H₉ | 6-CH₃ | 227–229 |

TABLE 7

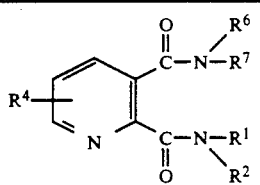

| No. | R¹ | R² | R⁴ | R⁶ | R⁷ | mp.(°C.) |
|---|---|---|---|---|---|---|
| 7.001 | sec.-C₄H₉ | H | 6-CH₃ | H | H | 131–133 |
| 7.002 | tert.-C₄H₉ | H | 6-Cl | H | H | 85 (decomp.) |
| 7.003 | sec.-C₄H₉ | H | 5-CH₃ | H | H | 119–123 as a mixture with 20% of isomeric 2-amide |
| 7.004 | i-C₄H₉ | H | 5-CH₃ | H | H | 118–122 as a mixture with 20% of isomeric 2-amide |

TABLE 8

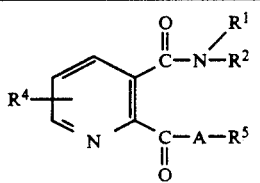

| No. | R¹ | R² | R⁴ | R⁵ | A | mp.(°C.) |
|---|---|---|---|---|---|---|
| 8.001 | i-C₄H₉ | H | 5-CH₃ | H | O | 125–129 (decomp.) |
| 8.002 | tert.-C₄H₉ | H | 6-tert.-C₄H₉ | CH₃ | O | 57–61 |

TABLE 9

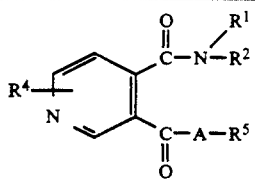

| No. | R¹ | R² | R⁴ | R⁵ | A | mp.(°C.) |
|---|---|---|---|---|---|---|
| 9.001 | tert.-C₄H₉ | H | 6-CH₂OCH₃ | H | O | 172–178 |
| 9.002 | tert.-C₄H₉ | H | 6-CH₂OCH₃ | CH₃ | O | 138–142 |

The compounds I'a, I'b and I'c, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I'a, I'b and I'c are suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone and water.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.1 to 90, % by weight of active ingredient. The active ingredients are used in a purity of from 90 to 100, and preferably from 95 to 100, %.

The pyridine derivatives I'a, I'b and I'c may be formulated for instance as follows:

I. 90 parts by weight of compound no. 3.003 is mixed with 10 parts by weight of N-methyl-alpha-pyrrolidone. A mixture is obtained which is suitable for application in the form of very fine drops.

II. 20 parts by weight of compound no. 3.003 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.004 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and I mole of castor oil. By pouring the solution into 100,000 parts by weight of water and finely distributing it therein, an aqueous dispersion is obtained containing 0.020% by weight of the active ingredient.

IV. 20 parts by weight of compound no. 3.003 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3.004 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.001 is intimately mixed with 97 parts by weight of particulate kaolin. A dust is obtained containing 3% by weight of the active ingredient.

VII. 30 parts by weight of compound no. 2.002 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 3.010 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5, preferably 0.01 to 2, kg of active ingredient per hectare.

In view of the numerous application methods possible, the compounds according to the invention may be used in a large number of crops for removing unwanted plant growth.

To increase the spectrum of action and to achieve synergistic effects, the compounds I'a, I'b and I'c may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the pyridine derivatives I'a, I'b and I'c, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

USE EXAMPLES

The herbicidal action of the pyridine derivatives I'a, I'b and I'c is demonstrated in greenhouse experiments:

The vessels employed were plastic flowerpots having a volume of 300 cm$^3$ and filled with a sandy loam containing about 3.01% humus. The seeds of the test plants were sown separately, according to species.

For the preemergence treatment, the active ingredients, suspended or emulsified in water, were applied through finely distributing nozzles to the surface of the soil immediately after the seeds had been sown. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were Abutilon theophrasti, Bromus inermis, Chenopodium album, Chrysanthemum coronarium and Stellaria media.

For instance pyridine derivatives 3.003 and 3.004, applied postemergence at a rate of 1.0 kg/ha, provided excellent control of unwanted plants.

We claim:

1. A pyridine derivative of the formula Ia,

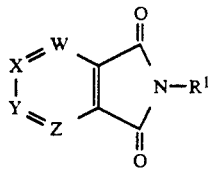

where

W, X, Y and Z are each C—$R^4$, N or N—O with the proviso that the ring contains only one heteroatom and one or two substituents $R^4$ which are different from hydrogen and the substituents $R^1$, and $R^4$ have the following meanings:

$R^1$ is unsubstituted $C_1$-$C_4$-alkoxy or $C_1$-$C_4$-alkoxy or $C_3$-$C_4$-alkyl which are substituted by one to three of the following groups: $C_1$-$C_4$-alkoxy, $C_1$-$C_4$-haloalkoxy, $C_1$-$C_4$-alkylthio, $C_1$-$C_4$-haloalkylthio, $C_1$-$C_4$-dialkylamino, $C_3$-$C_8$-cycloalkyl, or halogen;

$C_3$-$C_8$-cycloalkyl which is unsubstituted or is substituted by from one to three of the following groups: $C_1$-$C_4$-haloalkyl, $C_1$-$C_4$-alkoxy, $C_1$-$C_4$-haloalkoxy, halogen, nitro or cyano;

$C_3$-$C_6$-alkenyl which is unsubstituted or is substituted by from one three halogen substituents; or $C_3$-$C_6$-alkynyl which is unsubstituted or is substituted by from one to three halogen substituents;

$R^4$ is hydrogen, halogen, nitro, cyano or $C_1$-$C_6$-alkyl which is unsubstituted or substituted by from one to five halogen atoms and/or one or two of the following radicals: $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl or cyano;

benzyl which is unsubstituted or is substituted by from one to three of the following substituents: $C_1$-$C_4$-alkyl, $C_1$-$C_4$-haloalkyl, $C_1$-$C_4$-alkoxyl, $C_1$-$C_4$-haloalkoxy, $C_1$-$C_4$-alkylthio, $C_1$-$C_4$-haloalkylthio, halogen, cyano or nitro;

$C_3$-$C_6$-cycloalkyl which is unsubstituted or is substituted by from one to three $C_1$-$C_4$-alkyl or halogen substituents;

$C_2$-$C_6$-alkenyl which is unsubstituted or is substituted by from one to three halogen substituents and/or one $C_1$-$C_3$-alkoxy substituent, or one phenyl substitutent which may bear from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro;

$C_3$-$C_6$-alkynyl which is unsubstituted or is substituted by from one to three halogen or $C_1$-$C_3$-alkoxy substituents and/or one phenyl substituent which may bear from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro;

$C_1$-$C_4$-alkoxy, $C_1$-$C_4$-alkylthio, $C_1$-$C_4$-haloalkoxy, $C_1$-$C_4$-haloalkylthio, $C_2$-$C_5$-alkenyloxy, $C_2$-$C_5$-alkynloxy, $C_1$-$C_4$-alkylsulfinyl, $C_1$-$C_4$-alkylsulfonyl or $C_1$-$C_4$-haloalkylsulfonyl;

phenoxy or phenylthio, each of which is unsubstituted or is substituted by from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro;

a 5- or 6-membered heterocyclic radical with one or two heteroatoms selected from the group consisting of:

tetrahydrofuryl, tetrahydropyranyl, furyl, thienyl, thiazolyl, pyrazolyl, pyrrolyl, pyridyl, morpholino, piperidino or pyrimidyl, or said radicals substituted by from one to three methyl, ethyl, chlorine or fluorine substituents; or phenyl which is unsubstituted or is substituted by from one to three of the following substituents: $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, nitro, or cyano;

with the proviso that X and Z in formula Ia are not simultaneously C—$R^4$, $R^4$ being halogen, or independently of each other are C—$R^4$, $R^4$ being halogen or hydroxyl, when Y is N, and that X in formula Ia is not C—$R^4$, $R^4$ being phenyl, when Y is N, with the further proviso that if Z is nitrogen and $R^1$ is a substituted or unsubstituted cycloalkyl group, W is a group C—$R^4$ wherein $R^4$ does not stand for hydrogen, halogen, hydroxy or methyl and their agriculturally utilizable salts.

2. A process for combatting the growth of unwanted plants, wherein the unwanted plants and/or their habitat are treated with a herbicidally effective amount of a pyridine derivative as defined in claim 1.

3. A herbicidal composition comprising a carrier and a herbicidally effective amount of a pyridine derivative as defined in claim 1.

* * * * *